(12) United States Patent
Newkirk et al.

(10) Patent No.: US 7,798,456 B2
(45) Date of Patent: Sep. 21, 2010

(54) TRANSFERABLE PATIENT CARE EQUIPMENT SUPPORT

(75) Inventors: David C. Newkirk, Lawrenceburg, IN (US); Cristian J. Daugbjerg, Novato, CA (US)

(73) Assignee: Hill-Rom Services, Inc., Wilmington, DE (US)

( * ) Notice: Subject to any disclaimer, the term of this patent is extended or adjusted under 35 U.S.C. 154(b) by 328 days.

(21) Appl. No.: 11/842,578

(22) Filed: Aug. 21, 2007

(65) Prior Publication Data

US 2009/0050756 A1 Feb. 26, 2009

(51) Int. Cl.
*A47B 96/06* (2006.01)
*A47G 29/00* (2006.01)

(52) U.S. Cl. .............. 248/219.1; 248/218.4; 248/276.1

(58) Field of Classification Search .................... 24/514; 248/276.1, 125.8, 229.2, 229.23, 229.13, 248/229.1, 218.4, 219.1
See application file for complete search history.

(56) References Cited

U.S. PATENT DOCUMENTS

| 383,815 | A | | 5/1888 | Kilborn |
| 1,290,809 | A | | 1/1919 | Truax |
| 1,490,650 | A | | 4/1924 | Wagner |
| 1,919,114 | A | | 7/1933 | Ley |
| 2,063,924 | A | * | 12/1936 | Hanko ................. 248/229.23 |
| 2,470,524 | A | | 5/1949 | Scudder |
| 2,497,425 | A | | 2/1950 | Terry |
| 2,673,771 | A | | 3/1954 | Krewson |
| 2,696,963 | A | | 12/1954 | Sheperd |
| 2,995,332 | A | * | 8/1961 | Davis ................. 248/229.13 |
| 3,004,743 | A | | 10/1961 | Wenger |
| 3,213,877 | A | | 10/1965 | May et al. |
| 3,431,937 | A | | 3/1969 | Hettlingr et al. |
| 3,552,577 | A | | 1/1971 | Latham, Jr. |
| 3,674,294 | A | | 7/1972 | Kirkham |
| 3,709,556 | A | | 1/1973 | Allard et al. |
| 3,814,023 | A | | 6/1974 | Stantial |
| 4,005,844 | A | | 2/1977 | Richmond |
| 4,094,484 | A | | 6/1978 | Galione |
| 4,113,222 | A | | 9/1978 | Frinzel |
| 4,190,224 | A | | 2/1980 | LeBlanc et al. |
| 4,225,104 | A | | 9/1980 | Larson |

(Continued)

FOREIGN PATENT DOCUMENTS

DE 92 04 321.6 5/1992

(Continued)

OTHER PUBLICATIONS

"Pump Star User's Manual", The Headwall Company, Modular Services Company, Dec. 22, 2005, 11 pages.

(Continued)

*Primary Examiner*—Amy J Sterling
(74) *Attorney, Agent, or Firm*—Barnes & Thornburg LLP

(57) ABSTRACT

A patient care equipment support is transferable between a first device having a first coupling member and a second device having a second coupling member. The equipment support comprises an equipment supporting portion configured to support patient care equipment and a coupler coupled to the equipment supporting portion and having first and second clamps. The first clamp is configured to grip the first coupling member and the second clamp is configured to grip the second coupling member.

17 Claims, 24 Drawing Sheets

U.S. PATENT DOCUMENTS

| | | | |
|---|---|---|---|
| 4,262,874 A | 4/1981 | Seigh | |
| D260,816 S | 9/1981 | Zissimopoulos et al. | |
| 4,339,104 A | 7/1982 | Weidman | |
| 4,378,014 A | 3/1983 | Elkow | |
| 4,489,454 A | 12/1984 | Thompson | |
| 4,511,157 A | 4/1985 | Wilt, Jr. | |
| 4,511,158 A | 4/1985 | Varga et al. | |
| 4,559,036 A | 12/1985 | Wunsch | |
| 4,600,209 A | 7/1986 | Kerr, Jr. | |
| 4,616,797 A | 10/1986 | Cramer | |
| D289,604 S | 5/1987 | Gallant et al. | |
| 4,691,397 A | 9/1987 | Netzer | |
| 4,718,892 A | 1/1988 | Yung-Ho | |
| 4,725,027 A | 2/1988 | Bekanich | |
| 4,729,576 A | 3/1988 | Roach | |
| 4,738,369 A | 4/1988 | Desjardins | |
| 4,744,536 A | 5/1988 | Bancalari | |
| 4,756,706 A | 7/1988 | Kerns et al. | |
| 4,795,122 A | 1/1989 | Petre | |
| 4,879,798 A | 11/1989 | Petre | |
| 4,892,279 A | 1/1990 | Lafferty et al. | |
| 4,901,967 A | 2/1990 | Petre | |
| 4,905,882 A | 3/1990 | Ross | |
| 4,905,944 A | 3/1990 | Jost et al. | |
| 4,925,444 A | 5/1990 | Orkin et al. | |
| 4,945,592 A | 8/1990 | Sims et al. | |
| 4,966,340 A | 10/1990 | Hunter | |
| 4,969,768 A | 11/1990 | Young | |
| 4,997,150 A | 3/1991 | Mardollo | |
| 5,016,307 A | 5/1991 | Rebar | |
| 5,078,349 A | 1/1992 | Smith | |
| 5,083,807 A | 1/1992 | Bobb et al. | |
| 5,094,418 A | 3/1992 | McBarnes, Jr. et al. | |
| 5,110,076 A | 5/1992 | Snyder et al. | |
| 5,112,019 A | 5/1992 | Metzler et al. | |
| 5,125,607 A | 6/1992 | Pryor | |
| 5,135,191 A | 8/1992 | Schmuhl | |
| 5,149,036 A | 9/1992 | Sheehan | |
| 5,207,642 A | 5/1993 | Orkin et al. | |
| 5,219,139 A | 6/1993 | Hertzler et al. | |
| 5,224,681 A | 7/1993 | Lundstrom | |
| 5,306,109 A | 4/1994 | Kreuzer et al. | |
| 5,319,816 A | 6/1994 | Ruehl | |
| 5,326,059 A | 7/1994 | Pryor et al. | |
| 5,337,992 A | 8/1994 | Pryor et al. | |
| 5,344,169 A | 9/1994 | Pryor et al. | |
| 5,366,191 A | 11/1994 | Bekanich | |
| 5,400,995 A | 3/1995 | Boyd | |
| 5,407,163 A | 4/1995 | Kramer et al. | |
| 5,421,548 A | 6/1995 | Bennett et al. | |
| 5,527,125 A | 6/1996 | Kreuzer et al. | |
| 5,556,065 A | 9/1996 | Wadley | |
| 5,588,166 A | 12/1996 | Burnett | |
| 5,618,090 A | 4/1997 | Montague et al. | |
| 5,636,823 A | 6/1997 | Boyd | |
| 5,647,491 A * | 7/1997 | Foster et al. | 211/113 |
| 5,657,884 A | 8/1997 | Zilincar, III | |
| 5,699,988 A | 12/1997 | Boettger et al. | |
| 5,704,577 A | 1/1998 | Gordon | |
| 5,857,685 A | 1/1999 | Phillips et al. | |
| 5,876,016 A | 3/1999 | Urban et al. | |
| 5,878,536 A | 3/1999 | Demmitt et al. | |
| 5,898,961 A | 5/1999 | Ambach et al. | |
| 5,924,658 A | 7/1999 | Shiery et al. | |
| 5,966,760 A | 10/1999 | Gallant et al. | |
| 5,987,670 A | 11/1999 | Sims et al. | |
| 6,056,249 A | 5/2000 | Fillom, Jr. | |
| 6,073,285 A | 6/2000 | Ambach et al. | |
| 6,109,572 A | 8/2000 | Urban et al. | |
| 6,155,743 A | 12/2000 | Chen | |
| 6,170,102 B1 | 1/2001 | Kreuzer | |
| 6,179,260 B1 | 1/2001 | Chanian | |
| 6,182,662 B1 | 2/2001 | McGhee | |
| 6,213,481 B1 | 4/2001 | Marchese et al. | |
| 6,231,016 B1 | 5/2001 | Slone | |
| 6,375,133 B1 | 4/2002 | Morrow | |
| 6,390,311 B1 | 5/2002 | Belokin | |
| 6,434,329 B1 | 8/2002 | Dube et al. | |
| 6,601,860 B2 | 8/2003 | Potter | |
| 6,619,599 B2 | 9/2003 | Elliott et al. | |
| 6,708,991 B1 | 3/2004 | Ortlieb | |
| 6,725,483 B2 | 4/2004 | Gallant et al. | |
| 2002/0047075 A1 * | 4/2002 | Metz et al. | 248/229.1 |
| 2002/0104934 A1 | 8/2002 | Elliott et al. | |
| 2003/0014817 A1 | 1/2003 | Gallant et al. | |
| 2004/0199996 A1 | 10/2004 | Newkirk et al. | |
| 2005/0000019 A1 | 1/2005 | Newkirk et al. | |
| 2005/0253034 A1 | 11/2005 | Bally et al. | |
| 2006/0249641 A1 * | 11/2006 | Bally et al. | 248/229.2 |

FOREIGN PATENT DOCUMENTS

| | | |
|---|---|---|
| DE | 92 04 3216 U1 | 7/1992 |
| EP | 0 943 306 B1 | 9/1999 |
| EP | 1 243 900 A2 | 9/2002 |
| GB | 1 061 383 | 3/1967 |
| WO | 00/09061 | 2/2000 |

OTHER PUBLICATIONS

"Modular Pump Star", The Headwall Company, Modular Services Company, 2005, 4 pages.

* cited by examiner

US 7,798,456 B2

TRANSFERABLE PATIENT CARE EQUIPMENT SUPPORT

FIELD OF THE INVENTION

The present disclosure relates to a patient care equipment support, and more particularly relates to a transferable patient care equipment support.

BACKGROUND OF THE INVENTION

Hospitalized patients often require patient care equipment to be in close proximity during hospital care. Such patient care equipment is typically supported on a patient care equipment support such as, a rack, shelf system, cabinet, or the like. Examples of patient care equipment include, but are not limited to, the following: heart monitoring equipment, medical gas delivery equipment, infusion management equipment, intra-venous bags, equipment monitors, patient monitors, defibrillators, IV poles, and the like, many of which directly connect to the patient via lines or tubes.

It is desirable that patient care equipment is transferable between a patient support, such as a hospital bed, a support structure, such as a ceiling or wall-mounted equipment support arm, and a wheeled cart or stand. An illustrative patient care equipment support that is transferable between a hospital bed, a service column and a wheeled stand is disclosed in a U.S. Patent Application, Publication Number US-2006-0242763-A1, which application is hereby incorporated by reference herein.

SUMMARY OF THE INVENTION

The present invention comprises an apparatus or a method having one or more of the features recited in the claims or one or more of the following features, which alone or in any combination may comprise patentable subject matter:

A patient care equipment support may be transferable between a first device, such as a hospital bed having a first coupling member, a second device, such as an arm system having a second coupling member, and a third device, such as a wheeled cart having a third coupling member. The equipment support may comprise an equipment supporting portion configured to support patient care equipment and a coupler coupled to the equipment supporting portion and having first and second clamps. The coupler may comprise a post that extends downwardly from the equipment supporting portion and the first and second clamps may be coupled to the post on first and second sides of the post.

The first clamp may grip the first coupling member of the first device when the equipment support is carried by the first device. The equipment support may be transferred from the first device to the second device when the second clamp grips the second coupling member of the second device and the first clamp releases the first coupling member of the first device to allow the first device to move away from the second device (or to allow the second device to move away from the first device). The equipment support may be transferred from the second device to the third device when the first clamp grips the third coupling member of the third device and the second clamp releases the second coupling member of the second device to allow the third device to move away from the second device (or vice versa).

The equipment support may be transferred from the third device to the first device when the second clamp grips the first coupling member of the first device and the first clamp releases the third coupling member of the third device to allow the first device to move away from the third device (or vice versa). Thus, the equipment support may be transferred from the first device to the second device to the third device and back to the first device, in any order.

The coupler may include a mounting block. The first clamp may include a first jaw and a first handle coupled to a first side of the mounting block and a first link coupled to the first jaw and coupled to the first handle. The first jaw may move between a closed position and an opened position as the first handle moves between a closed position and an opened position. The second clamp may include a second jaw and a second handle coupled to a second side of the mounting block and a second link coupled to the second jaw and coupled to the second handle. The second jaw may move between a closed position and an opened position as the second handle moves between a closed position and an opened position.

The mounting block may have a bore through which the post extending downwardly from the equipment supporting portion may extend. The first jaw may be coupled to the first side of the mounting block for pivoting movement about a first pivot pin. The first handle may be coupled to the first side of the mounting block for pivoting movement about a second pivot pin. The first link may have a first end coupled to the first jaw for pivoting movement about a third pivot pin. The first link may have a second end coupled to the first handle for pivoting movement about a fourth pivot pin. The mounting block, the first jaw, the first handle, and the first link may form a four bar linkage.

The second jaw may be coupled to the second side of the mounting block for pivoting movement about a fifth pivot pin. The second handle may be coupled to the second side of the mounting block for pivoting movement about a sixth pivot pin. The second link may have a first end coupled to the second jaw for pivoting movement about a seventh pivot pin. The second link may have a second end coupled to the second handle for pivoting movement about an eighth pivot pin. The mounting block, the second jaw, the second handle, and the second link may form a four bar linkage.

The first coupling member of the first device may comprise a first post that is configured to be received in a first post-receiving cavity defined by the first jaw and the mounting block when the first jaw is moved to the opened position in response to the first handle moving to the opened position. The first post may be clamped between the first jaw and the mounting block when the first jaw moves to the closed position after receiving the first post in the first post-receiving cavity in response to the first handle moving to the closed position.

The second coupling member of the second device may comprise a second post that is configured to be received in a second post-receiving cavity defined by the second jaw and the mounting block when the second jaw is moved to the opened position in response to the second handle moving to the opened position. The second post may be clamped between the second jaw and the mounting block when the second jaw moves to the closed position after receiving the second post in the second post-receiving cavity in response to the second handle moving to the closed position.

The equipment support may further comprise a lock configured such that in case only one of the posts is received in one of the post-receiving cavities and the associated handle is moved to the closed position, said one of the posts is locked to the equipment support coupler, and such that in case any two of the three posts are received in the two post-receiving cavities, both of the handles are unlocked so that respective engagements of both posts and the equipment support coupler are releasable.

The lock may comprise a first slider and a second slider. Each slider may be movable between a retracted latching position and an extended unlatching position. Both sliders may be spring biased toward their respective retracted positions. When the first slider is in its retracted position, a first tab of the first slider may project into the second post-receiving cavity and a first hook of the first slider may engage the third pivot pin to lock the first handle in the closed position. Likewise, when the second slider is in its retracted position, a second tab of the second slider may project into the first post-receiving cavity and a second hook of the second slider may engage the seventh pivot pin to lock the second handle in the closed position.

The lock may be configured such that, when the first post is received in the first post-receiving cavity, the first post pushes the second tab out of the first post-receiving cavity against the spring bias to shift the second slider to its extended position to disengage the second hook from engagement with the seventh pivot pin to unlock the second handle to allow it to move between its open and closed positions, and such that, when the second post is received in the second post-receiving cavity, the second post pushes the first tab out of the second post-receiving cavity against the spring bias to shift the first slider to its extended position to disengage the first hook from engagement with the third pivot pin to unlock the first handle to allow it to move between its open and closed positions.

Each slider may have two slots through which the first and fifth pivot pins extend so that the sliders may shift between their respective retracted positions and unlocking positions. The lock may further comprise a spring that is situated in a state of compression between the inwardly-facing edges of the first and second tabs to bias the first and second sliders to their respective retracted locking positions so that the first tab projects into the second post-receiving cavity and the second tab projects into the first post-receiving cavity, so that the first hook engages the third pivot pin to lock the first handle in its closed position and so that the second hook engages the seventh pivot pin to lock the second handle in its closed position.

In other embodiments, the equipment support may comprise a latch that is movable to the first side when the first handle is in the closed position to lock the first handle and the first jaw in their respective closed positions and to unlock the second handle to allow it to move between its closed and opened positions and the latch may be movable to the second side when the second handle is in the closed position to lock the second handle and the second jaw in their respective closed positions and to unlock the first handle to allow it to move between its closed and opened positions. The latch may not be movable to the first side when the first handle is in the opened position and the latch may not be movable to the second side when the second handle is in the opened position.

The equipment supporting portion may comprise an upper cross bar, a lower cross bar and a pair of telescoping outer posts extending between the upper and lower cross bars. A central post may also extend between the upper and lower cross bars. The first and second clamps may be coupled to a lower portion of the central post that extends below the lower member.

Each outer post may comprise a first portion and a second portion that may telescope into and out of the first portion and a lock movable between a releasing position allowing the second portion to telescope into and out of the first portion and a locking position preventing the second portion from telescoping relative to the first portion. Each outer post may further comprise a plurality of IV bag hooks coupled to an upper end of the second portion. The equipment support may further comprise a pair of handles extending forwardly from the lower member adjacent to the outer posts.

In some embodiments, an apparatus is provided for use with a patient care equipment support having a downwardly-extending post. The apparatus may comprise a support, an arm extending outwardly from the support and a clamp carried by the arm. The clamp may be configured to grip the downwardly-extending post of the equipment support when the equipment support is carried by the apparatus. In some embodiments, the apparatus may comprise a patient support, such as a hospital bed. The bed may comprise a lower frame supported on casters and an upper frame supported above the lower frame and movable between a raised position and a lowered position. The arm may extend outwardly from the upper frame and the clamp may be coupled to the arm.

In other embodiments, the apparatus may comprise an arm system. The arm system may comprise a service head that extends downwardly from a ceiling-mounted radial arm. The arm may extend outwardly from the service head and the clamp may be coupled to the arm. In still other embodiments, the apparatus may comprise a wheeled cart. The cart may comprise a base supported on wheels and a telescoping column extending upwardly from the base. The arm may extend outwardly from the telescoping column and the clamp may be coupled to the arm.

In some embodiments, the clamp may comprise a movable jaw coupled to the arm, a handle coupled to the movable jaw, and a link coupled to the handle and coupled to the arm. The movable jaw may move between a closed position and an opened position as the handle moves between a closed position and an opened position.

The movable jaw may be coupled to the arm for pivoting movement about a first axis. The handle may be coupled to the movable jaw for pivoting movement about a second axis. The link may have a first end coupled to the handle for pivoting movement about a third axis and the link may have a second end coupled to the arm for pivoting movement about a fourth axis. The arm, the movable jaw, the handle, and the link may form a four bar linkage.

The downwardly-extending post of the equipment support may be configured to be received in a post-receiving cavity defined by the arm and the movable jaw when the movable jaw is open. The post may be clamped between the arm and the movable jaw when the movable jaw closes after receiving the post in the post-receiving cavity in response to the handle moving to its closed position.

The handle may pass through an over-the-center position as it moves from its opened position to its closed position. The post may exert an outward force on the movable jaw in a direction that may hold the handle in the past-over-the-center closed position. The apparatus may further comprise a latch movable between an unlatched position in which the handle is movable between its closed and opened positions and a latched position in which the handle is latched in the closed position.

In some embodiments, a patient care equipment support may comprise an upper member, a lower member, a pair of outer posts extending between the upper and lower members adjacent the opposite ends of the upper and lower members, a column extending between the upper and lower members between the two outer posts, and a first clevis including top and bottom flanges extending forwardly from the column. The top and bottom flanges of the first clevis may include top and bottom first openings. In some embodiments, the equipment support may further comprise a second clevis including top and bottom flanges extending rearwardly from the column. The top and bottom flanges of the second clevis may include top and bottom second openings.

The equipment support may be transferable between a first device and a second device. The first device may comprise a first support, a first arm extending outwardly from the first support, a first manual input coupled to the first arm, and a pair of oppositely-disposed top and bottom first pins that are movable relative to the first arm between respective retracted and extended positions in response to movement of the first manual input between a releasing position and a locking position. The top and bottom first pins may be configured to be received in the top and bottom first openings in the top and bottom flanges of the first clevis when the equipment support is carried by the first device and the first pins are disposed in their respective extended positions.

The second device may comprise a second support, a second arm extending outwardly from the second support, a second manual input coupled to the second arm, and a pair of oppositely-disposed top and bottom second pins that are movable relative to the second arm between respective retracted and extended positions in response to movement of the second manual input between a releasing position and a locking position. The top and bottom second pins may be configured to be received in the top and bottom second openings in the top and bottom flanges of the second clevis when the equipment support is carried by the second device and the second pins are disposed in their respective extended positions.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the following figures, in which.

DETAILED DESCRIPTION OF THE DRAWINGS

Figure 1:
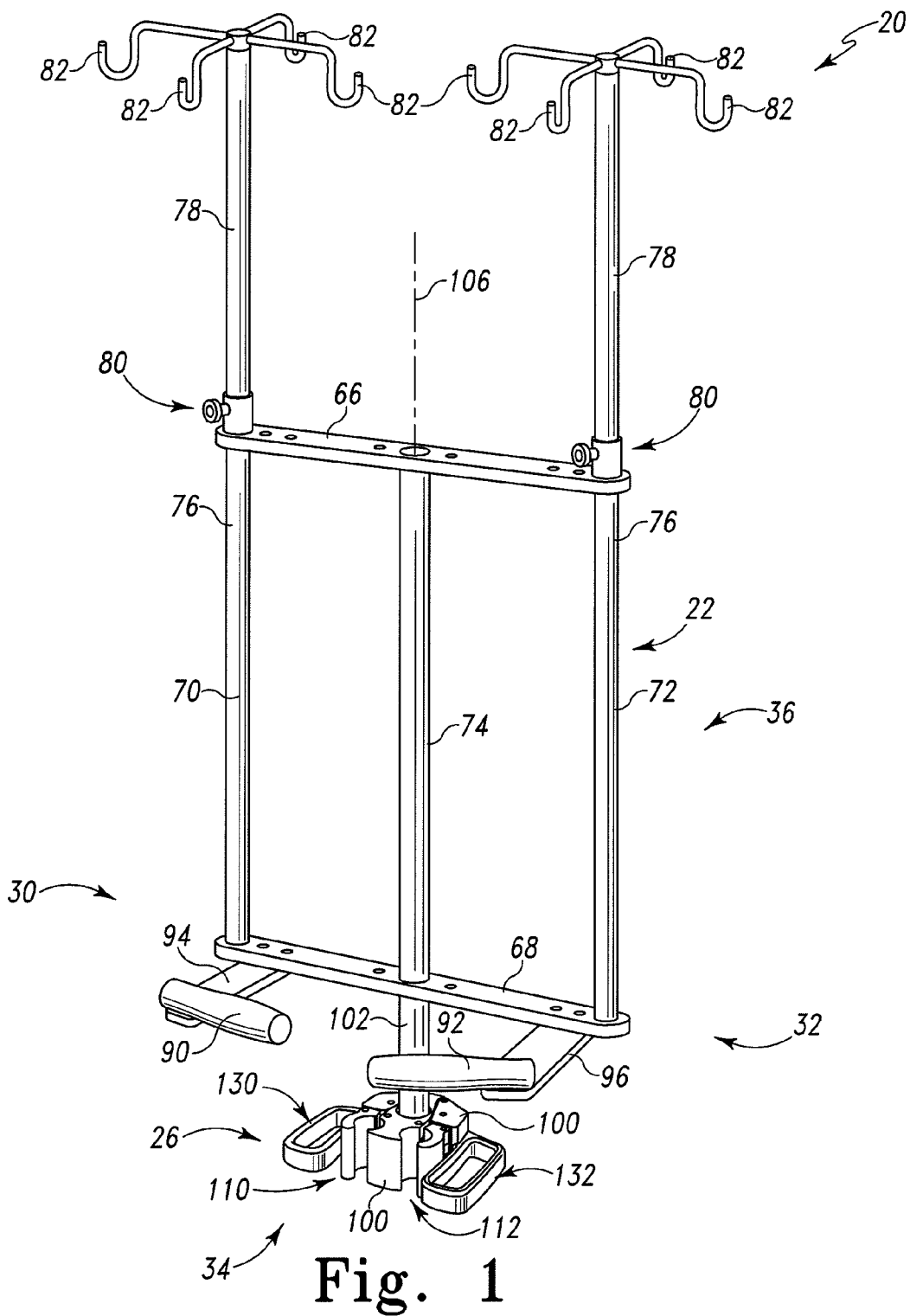
FIG. 1 is a perspective view of a patient care equipment support transferable between a first device, such as a hospital bed having a first upwardly-extending post, a second device, such as an arm system having a second upwardly-extending post, and a third device, such as a wheeled cart having a third upwardly-extending post, and showing the equipment support having an equipment supporting portion and a coupler coupled thereto, the equipment supporting portion having upper and lower cross bars, a pair of outer posts extending between the upper and lower cross bars, a central post extending between the upper and lower cross bars between the two outer posts, and a plurality of IV bag hooks coupled to upper ends of the outer posts, and the coupler having a mounting block coupled to a lower portion of the central post extending below the lower cross bar and first and second clamps coupled to first and second sides of the mounting block.

FIG. 1 shows an equipment support 20 having an equipment supporting portion 22 configured to support patient care equipment 24 (FIG. 16) and a coupler 26 coupled to equipment supporting portion 22. The equipment support 20 has a left or first side 30, a right or second side 32, a front or third side 34, and a rear or fourth side 36. As explained below, the equipment support 20 is directly transferable from a first device, such as a hospital bed 50 (FIG. 16) having an upwardly-extending first post 52 (FIG. 8), to a second device, such as an arm system 54 (FIG. 20) having an upwardly-extending second post 56 (FIG. 9), to a third device, such as a wheeled cart 58 (FIG. 10) having an upwardly-extending third post 60 (FIG. 10), and back to the hospital bed 50 having the upwardly-extending first post 52, in any order. For example, the equipment support 20 may be transferred from the bed 50 to the arm system 54 to the cart 58 and back to the bed 50 or from the bed 50 to the cart 58 to the arm system 54 and back to the bed 50.

It should be understood that although, in the illustrated embodiment, the equipment support 20 is supported by the bed 50, the arm system 54, and the wheeled cart 58, the equipment support 20 may very well be supported by other devices, such as a stretcher, a surgical table, a wheel chair, a wheeled stand, and the like, that have upwardly-extending posts. In the illustrated embodiment, the three upwardly-extending posts 52, 56, 60 are each circular in cross section and have substantially the same diameters. In other embodiments, however, the upwardly-extending posts 52, 56, 60 have non-circular cross sections and/or different diameters. It will be appreciated that such hospital beds and arm systems are well known and need not be discussed in detail herein. For example, the bed 50 may be of the type marketed by Hill-Rom as TotalCare™ hospital bed and the arm system 54 may be of the type marketed by Hill-Rom as Latitude™ Arm System.

As used in this description, the phrase "left or first side 30" will be used to denote the side of any referred-to object that is positioned to lie nearest the left or first side 30 of the equipment support 20, and the phrase "right or second side 32" will be used to denote the side of any referred-to object that is positioned to lie nearest the right or second side 32 of the equipment support 20. Likewise, the phrase "front or third side 34" will be used to denote the side of any referred-to object that is positioned to lie nearest the front or third side 34 of the equipment support 20, and the phrase "rear or fourth side 36" will be used to denote the side of any referred-to object that is positioned to lie nearest the rear or fourth side 36 of the equipment support 20.

As shown in FIG. 1, the equipment supporting portion 22 includes an upper cross bar 66, a lower cross bar 68, and a pair of telescoping outer posts 70, 72 extending between the upper and lower cross bars 66, 68 adjacent the opposite sides 30, 32 thereof. A central post 74 extends between the upper and lower cross bars 66, 68 between the two outer posts 70, 72. Each outer post 70, 72 has an outer tube 76 and an inner tube 78 that telescopes into and out of the outer tube 76. Each outer post 70, 72 includes a lock 80 that is movable between a releasing position allowing the inner tube 78 to telescope into and out of the outer tube 76 and a locking position blocking the inner tube 78 from telescoping relative to the outer tube 76. Each outer post 70, 72 includes a plurality of IV bag hooks 82 coupled to an upper end of the associated inner tube 78. A pair of handles 90, 92 are coupled to the lower cross bar 68 via respective handle bars 94, 96 that extend forwardly from the lower cross bar 68 adjacent the outer posts 70, 72.

As shown in FIGS. 1-5, the coupler 26 includes a mounting block 100 coupled to a lower portion 102 of the central post 74 that extends below the lower cross bar 68. The mounting block 100 has a central bore 104. The lower portion 102 of the post 74 is received in the bore 104 for pivoting movement about a vertical axis 106 to allow the equipment supporting portion 22 to rotate relative to the mounting block 100. The rotatable mounting of the equipment supporting portion 22 improves access to the patient care equipment 24 carried by the equipment support 20. Bushings 108 are interposed between the lower portion 102 of the post 74 and the mounting block 100 to facilitate pivoting movement of the post 74 relative to the mounting block 100. The coupler 26 further includes first and second clamps 110, 112 coupled to the mounting block 100 on the first and second sides 30, 32 thereof.

Figure 8:
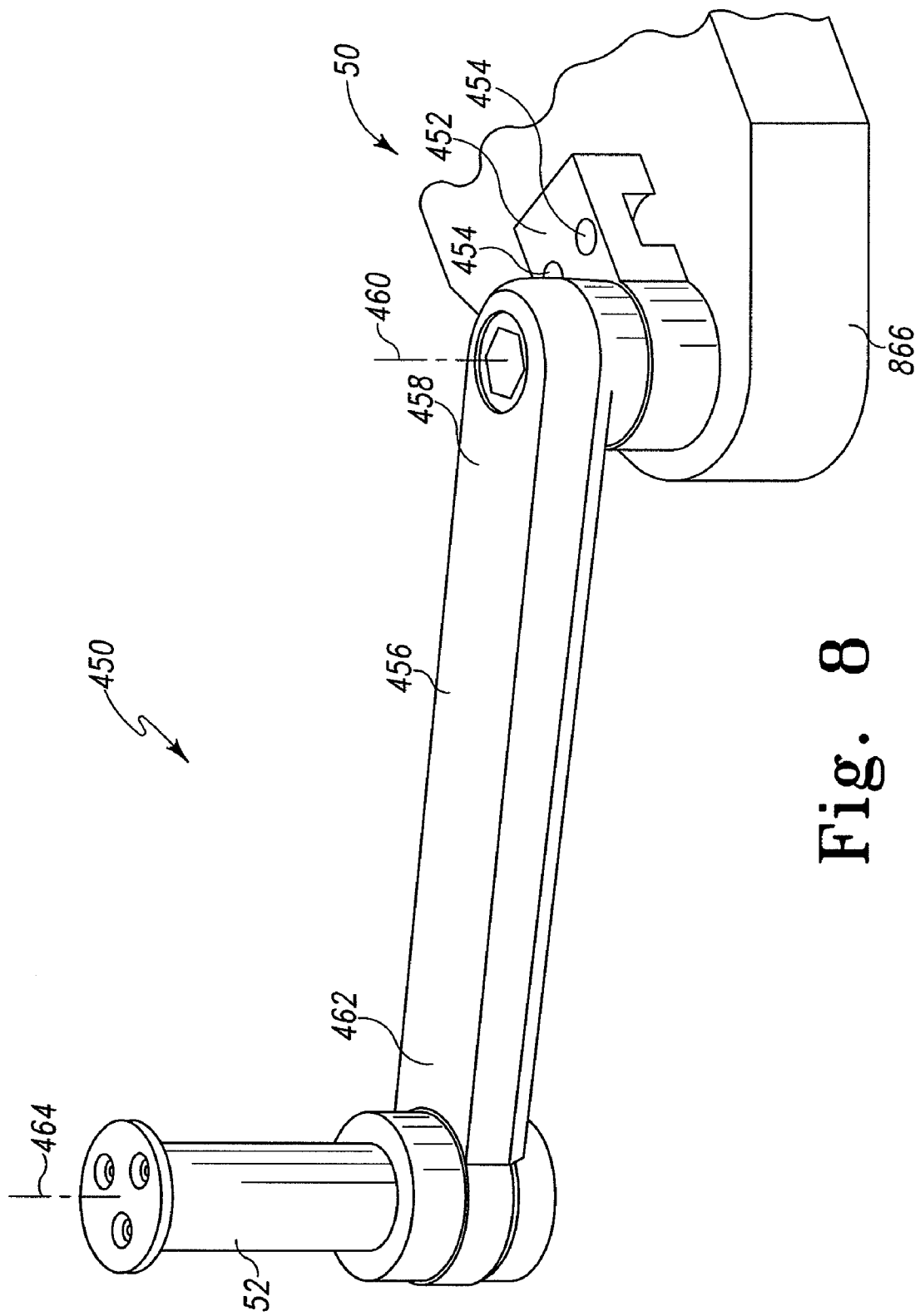
FIG. 8 is a perspective view of a bed mount showing the bed mount including a mounting bracket coupled to a corner bracket of the hospital bed, an arm having a proximal end coupled to the mounting bracket for pivoting movement about a first pivot axis, and the upwardly-extending first post coupled to a distal end of the arm for pivoting movement about a second pivot axis.

The first clamp 110 clamps the first post 52 of the bed 50 when the equipment support 20 is carried by the bed 50 (FIG. 8). The equipment support 20 is transferred from the bed 50 to the arm system 54 when the second clamp 112 clamps the second post 56 of the arm system 54 (FIG. 9) and the first clamp 110 releases the first post 52 of the bed 50 to allow the arm system 54 to move away from the bed 50 with the arm system 54 carrying the equipment support 20 (or to allow the bed 50 to move away from the arm system 54 with the arm system 54 carrying the equipment support 20). The equipment support 20 is transferred from the arm system 54 to the cart 58 when the first clamp 110 clamps the third post 60 of the cart 58 (FIG. 10) and the second clamp 112 releases the second post 56 of the arm system 54 to allow the cart 58 to move away from the arm system 54 with the cart 58 carrying the equipment support 20 (or to allow the arm system 54 to move away from the cart 58 with the cart 58 carrying the equipment support 20). The equipment support 20 is transferred from the cart 58 back to the bed 50 when the second clamp 112 clamps the first post 52 of the bed 50 and the first clamp 110 releases the third post 60 of the cart 58 to allow the cart 58 to move away from the bed 50 with the bed 50 carrying the equipment support 20 (or to allow the bed 50 to move away from the cart 58 with the bed 50 carrying the equipment support 20).

Figure 2:
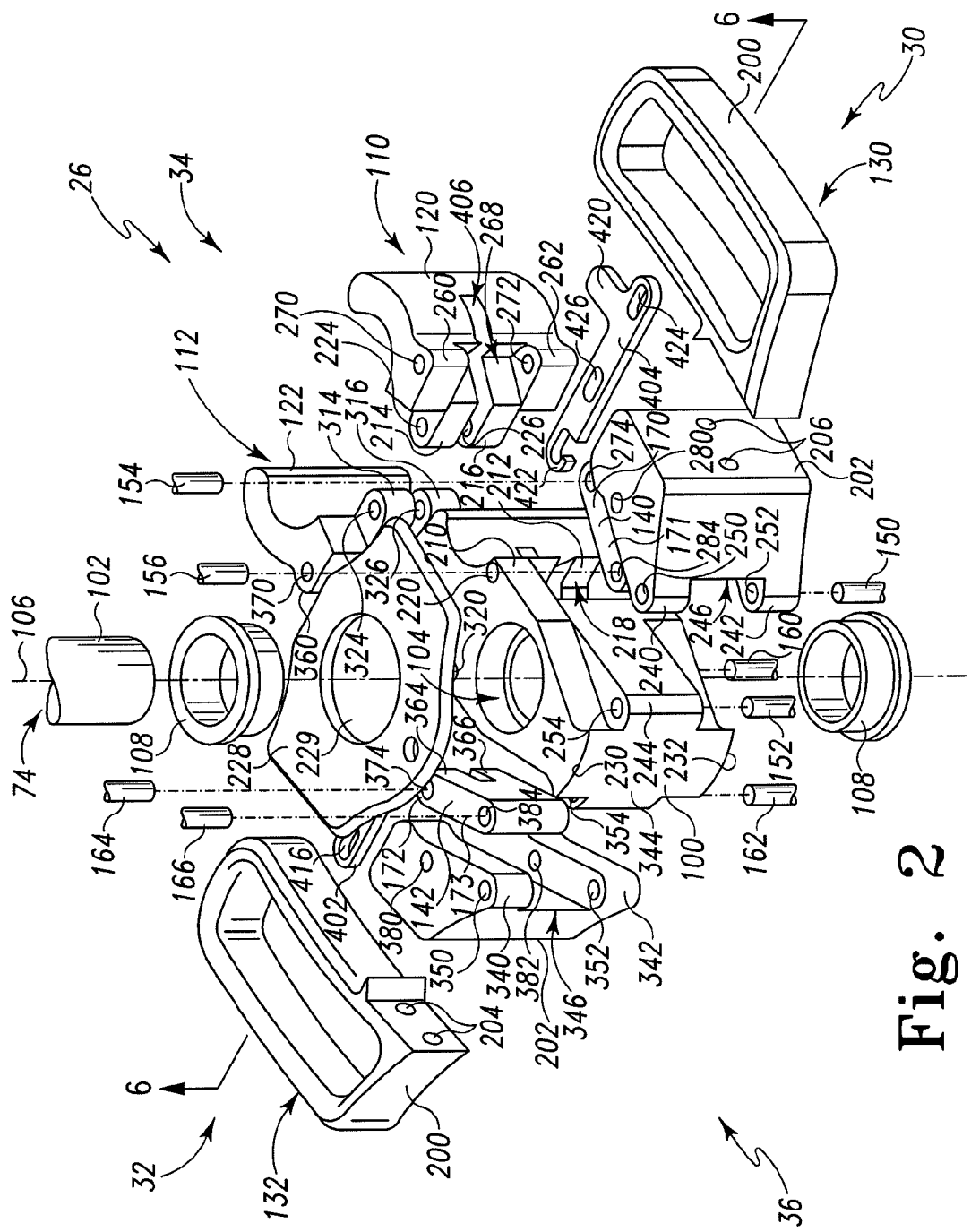
FIG. 2 is an exploded perspective view of the coupler showing the mounting block having a central bore for receiving the lower portion of the central post, the first clamp having a first jaw and a first handle coupled to the first side of the mounting block and a first link coupled to the first jaw and coupled to the first handle, the second clamp having a second jaw and a second handle coupled to the second side of the mounting block and a second link coupled to the second jaw and coupled to the second handle, the first jaw moving between a closed position and an opened position as the first handle moves between a closed position and an opened position, the second jaw moving between a closed position and an opened position as the second handle moves between a closed position and an opened position, the first jaw and the mounting block defining a first post-receiving cavity and the second jaw and the mounting block defining a second post-receiving cavity.
Figure 3:
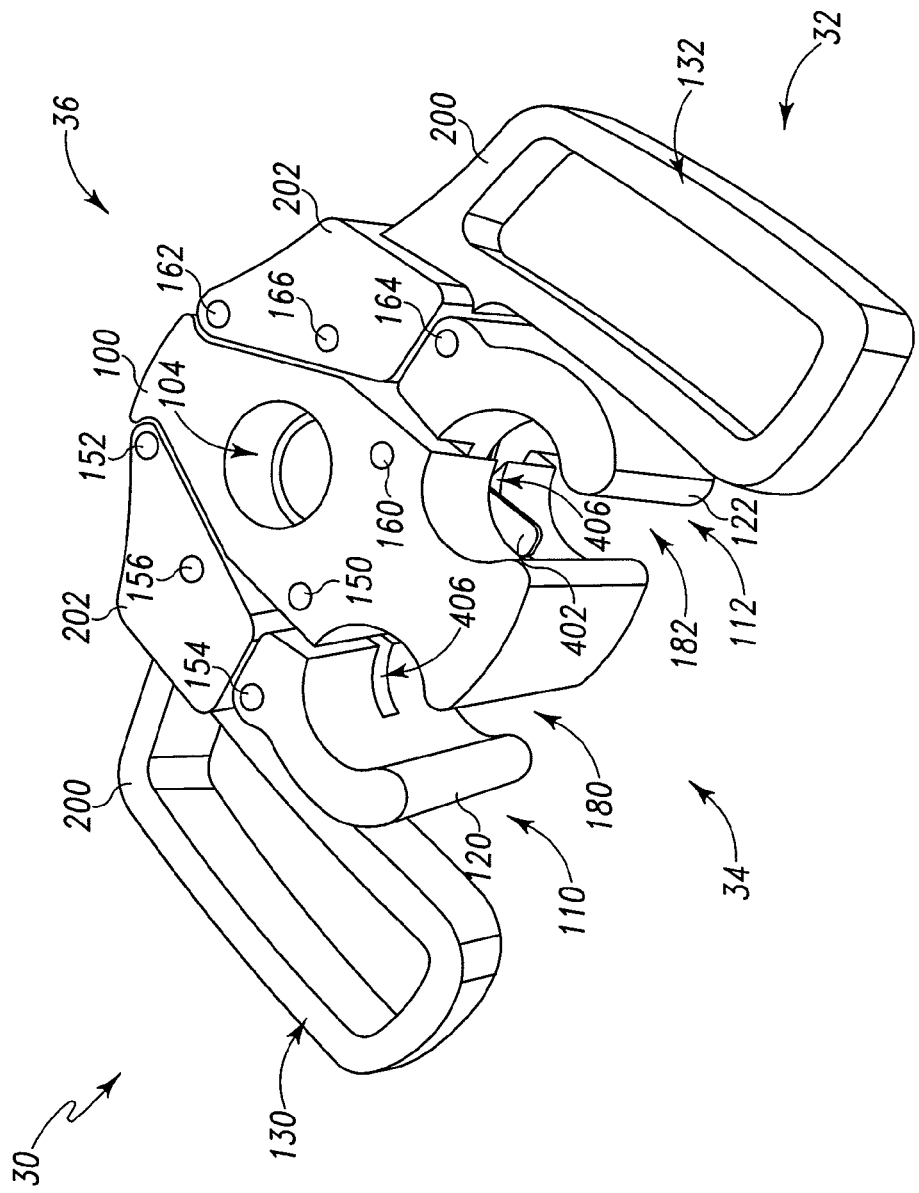
FIG. 3 is an enlarged perspective view of the coupler showing the first and second jaws moved to their respective closed positions in response to the first and second handles moving to their respective closed positions.
Figure 4:
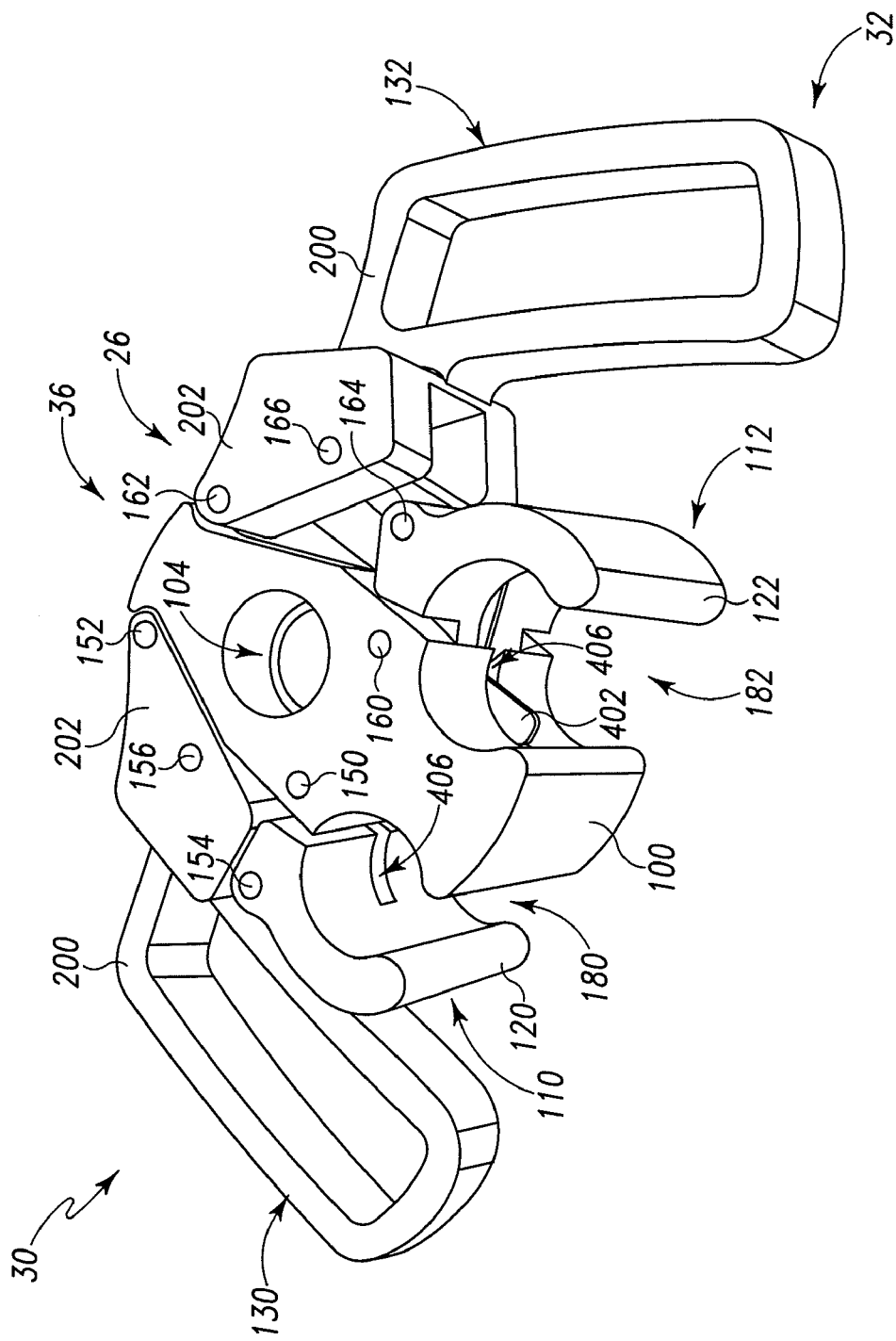
FIG. 4 is an enlarged perspective view similar to FIG. 3 showing the second jaw moved to the opened position in response to the second handle moving to the opened position and the first jaw and the first handle remaining in their respective closed positions.

As shown in FIGS. 1-5, the first clamp 110 includes a first jaw 120 and a first handle 130 coupled to the first side 30 of the mounting block 100 and a first link 140 coupled to the first jaw 120 and coupled to the first handle 130. The mounting block 100, the first jaw 120, the first handle 130, and the first link 140 form a first 4-bar linkage. The second clamp 112 includes a second jaw 122 and a second handle 132 coupled to the second side 32 of the mounting block 100 and a second link 142 coupled to the second jaw 122 and coupled to the second handle 132. The mounting block 100, the second jaw 122, the second handle 132, and the second link 142 form a second 4-bar linkage. The first jaw 120 moves between a closed position (FIG. 3) and an opened position (shown in FIG. 4 with respect to the second jaw 122) as the first handle 122 moves between a closed position (FIG. 3) and an opened position (shown in FIG. 4 with respect to the second handle 132). The second jaw 122 moves between a closed position (FIG. 3) and an opened position (FIG. 4) as the second handle 132 moves between a closed position (FIG. 3) and an opened position (FIG. 4). The first jaw 120 and the first side 30 of the mounting block 100 define a first post-receiving cavity 180. The second jaw 122 and the second side 32 of the mounting block 100 define a second post-receiving cavity 182.

In the illustrated embodiment, the two clamps 110, 112 are generally mirror images of each other. Each post-receiving cavity 180, 182 is configured to receive any of the three posts 52, 56, 60 of the bed 50, the arm system 54 and the cart 58, shown in FIGS. 8-10 respectively. Thus, the first post 52 of the bed 50 may be clamped in the first post-receiving cavity 180 or the second post-receiving cavity 182. Likewise, the second post 56 of the arm system 54 may be clamped in the first post-receiving cavity 180 or the second post-receiving cavity 182 and the third post 60 of the cart 58 may be clamped in the first post-receiving cavity 180 or the second post-receiving cavity 182.

The first jaw 120 is coupled to the first side 30 of the mounting block 100 for pivoting movement about a first pivot pin 150. The first handle 130 is coupled to the first side 30 of the mounting block 100 for pivoting movement about a second pivot pin 152. The first link 140 has a first end 170 coupled to the first jaw 120 for pivoting movement about a third pivot pin 154. The first link 140 has a second end 171 coupled to the first handle 130 for pivoting movement about a fourth pivot pin 156. The second jaw 122 is coupled to the second side 32 of the mounting block 100 for pivoting movement about a fifth pivot pin 160. The second handle 132 is coupled to the second side 32 of the mounting block 100 for pivoting movement about a sixth pivot pin 162. The second link 142 has a first end 172 coupled to the second jaw 122 for pivoting movement about a seventh pivot pin 164. The second link 142 has a second end 173 coupled to the second handle 132 for pivoting movement about an eighth pivot pin 166. The pivot pins 150, 152, 154, 156, 160, 162, 164, 166 are prevented from falling off by cover plates 228 secured to top and bottom surfaces 230, 232 of the mounting block 100. The lower portion 102 of the central post 74 extends through slightly-oversized openings 229 in the cover plates 228. In some embodiments, however, the upper and lower ends of the pivot pins 150, 152, 154, 156, 160, 162, 164, 166 have circumferential grooves for receiving respective C-washers to retain the pivot pins 150, 152, 154, 156, 160, 162, 164, 166 in place.

As shown in FIG. 2, in the illustrated embodiment, each handle 130, 132 comprises a handle grip 200 and a handle mount 202. A caregiver grasps the handle grip 200 of the handle 130, 132 to move the handle 130, 132 between its closed and opened positions. The handle mount 202 couples the associated handle 130, 132 to the mounting block 100 as shown in FIGS. 2-4. The handle grips 200 are secured to the associated handle mounts 202 by any suitable means, such as screws (not shown) that extend through slightly oversized openings 204 (FIG. 2) in the handle grips 200 and screwed into threaded openings 206 (FIG. 2) in the associated handle mounts 202. In other embodiments, the handle grips 200 are integrally formed with the handle mounts 202.

As shown in FIG. 2, the mounting block 100 is formed to include a pair of spaced-apart lugs 210, 212 that extend generally horizontally outwardly from the first side 30 of the mounting block 100. The first jaw 120 is formed to include a pair of spaced-apart lugs 214, 216 that extend generally horizontally outwardly from the second side 32 of the first jaw 120. The spaced-apart lugs 210, 212 of the mounting block 100 define a cavity 218 in which the lugs 214, 216 of the first jaw 120 are received for pivoting movement. The vertical spacing between the inner surfaces of the lugs 210, 212 of the mounting block 100 is slightly larger than the vertical spacing between the outer surfaces of the lugs 214, 216 of the first jaw 120. As used in this description, the phrase "inner surfaces" will be used to denote downwardly and upwardly-facing inner surfaces of any referred-to object. Likewise, the phrase "outer surfaces" will be used to denote upwardly and downwardly-facing outer surfaces of any referred-to object. The first pivot pin 150 extends through an opening 220 in the upper lug 210 of the mounting block 100, extends through openings 224, 226 in the lugs 214, 216 of the first jaw 120, and then extends through an opening 220 in the lower lug 212 of the mounting block 100.

The handle mount 202 of the first handle 130 is formed to include a pair of spaced-apart lugs 240, 242 that extend generally horizontally outwardly from the second side 32 of the first handle 130. The mounting block 100 is formed to include a lug 244 that extends generally horizontally outwardly from the first side 30 of the mounting block 100. The lugs 240, 242 of the first handle 130 define a cavity 246 in which the lug 244 of the mounting block 100 is received for pivoting movement. The vertical spacing between the inner surfaces of the lugs 240, 242 of the first handle 130 is slightly larger than the vertical spacing between the outer surfaces of the lug 244 of the mounting block 100. The second pivot pin 152 extends through an opening 250 in the upper lug 240 of the first handle 130, extends through opening 254 in the lug 244 of the mounting block 100, and then extends through an opening 252 in the lower lug 242 of the first handle 130.

The first jaw 120 is formed to include a pair of spaced-apart lugs 260, 262 that extend generally horizontally outwardly from the first side 30 of the first jaw 120. The first link 140 is formed to include a pair of spaced-apart lugs (similar to lugs 364, 366 of the second link 142) that extend generally horizontally outwardly from the first end 170 of the first link 140. The spaced-apart lugs 260, 262 of the first jaw 120 define a cavity 268 in which the lugs of the first link 140 are received for pivoting movement. The vertical spacing between the inner surfaces of the lugs 260, 262 of the first jaw 120 is slightly larger than the vertical spacing between the outer surfaces of the lugs of the first link 140 (similar to lugs 364, 366 of the second link 142). The third pivot pin 154 extends through an opening 270 in the upper lug 260 of the first jaw 120, extends through openings 274 in the lugs of the first link 140, and then extends through an opening 272 in the lower lug 262 of the first jaw 120.

The second end 171 of the first link 140 is received in the cavity 246 defined by the spaced-apart lugs 240, 242 of the first handle 130 for pivoting movement. The vertical spacing between the inner surfaces of the lugs 240, 242 of the first handle 130 is slightly larger than the vertical spacing between the outer surfaces of the first link 140. The fourth pivot pin 156 extends through an opening 280 in the upper lug 240 of the first handle 130, extends through opening 284 in the first link 140, and then extends through an opening in the lower lug 242 of the first handle 130 (similar to the opening 382 in the lower lug 342 of the second handle 132).

As shown in FIG. 2, the mounting block 100 is formed to include a pair of spaced-apart lugs (similar to the spaced-apart lugs 210, 212 on the first side 30 of the mounting block 100) that extend generally horizontally outwardly from the second side 32 of the mounting block 100. The second jaw 122 is formed to include a pair of spaced-apart lugs 314, 316 that extend generally horizontally outwardly from the first side 30 of the second jaw 120. The spaced-apart lugs of the mounting block 100 (similar to the spaced-apart lugs 210, 212 of the mounting block 100) define a cavity (similar to the cavity 218 defined by the spaced-apart lugs 210, 212 of the mounting block 100) in which the lugs 314, 316 of the second jaw 122 are received for pivoting movement. The vertical spacing between the inner surfaces of the lugs of the mounting block 100 (similar to the lugs 210, 212 of the mounting block 100) is slightly larger than the vertical spacing between the outer surfaces of the lugs 314, 316 of the second jaw 122. The fifth pivot pin 160 extends through an opening 320 in the upper lug on the second side 32 of the mounting block 100 (similar to the upper lug 210 on the first side 30 of the mounting block 100), extends through openings 324, 326 in the lugs 314, 316 of the second jaw 122, and then extends through an opening 320 in the lower lug of the mounting block 100 (similar to the lower lug 212 of the mounting block 100).

The handle mount 202 of the second handle 132 is formed to include a pair of spaced-apart lugs 340, 342 that extend generally horizontally outwardly from the first side 30 of the second handle 132. The mounting block 100 is formed to include a lug 344 that extends generally horizontally outwardly from the second side 32 of the mounting block 100. The lugs 340, 342 of the second handle 132 define a cavity 346 in which the lug 344 of the mounting block 100 is received for pivoting movement. The vertical spacing between the inner surfaces of the lugs 340, 342 of the second handle 132 is slightly larger than the vertical spacing between the outer surfaces of the lug 344 of the mounting block 100. The sixth pivot pin 162 extends through an opening 350 in the upper lug 340 of the second handle 132, extends through opening 354 in the lug 344 of the mounting block 100, and then extends through an opening 352 in the lower lug 342 of the second handle 132.

The second jaw 122 is formed to include a pair of spaced-apart lugs 360 that extend generally horizontally outwardly from the second side 32 of the second jaw 122 (similar to the spaced-apart lugs 260, 262 on the first side 30 of the first jaw 120). The second link 142 is formed to include a pair of spaced-apart lugs 364, 366 that extend generally horizontally outwardly from the first end 172 of the second link 142. The spaced-apart lugs 360 of the second jaw 122 define a cavity (similar to the cavity 268 defined by the spaced-apart lugs 260, 262 on the first side 30 of the first jaw 120) in which the lugs 364, 366 of the second link 142 are received for pivoting movement. The vertical spacing between the inner surfaces of the lugs 360 of the second jaw 122 is slightly larger than the vertical spacing between the outer surfaces of the lugs 364, 366 of the second link 142. The seventh pivot pin 164 extends through an opening 370 in the upper lug 360 of the second jaw 122, extends through openings 374 in the lugs 364, 366 of the second link 142, and then extends through an opening in the lower lug 362 of the second jaw 122 (similar to the opening 272 in the lower lug 262 of the first jaw 120).

The second end 173 of the second link 142 is received in the cavity 346 defined by the spaced-apart lugs 340, 342 of the handle mount 202 of of the second handle 132 for pivoting movement. The vertical spacing between the inner surfaces of the lugs 340, 342 of the second handle 132 is slightly larger than the vertical spacing between the outer surfaces of the second link 142. The eighth pivot pin 166 extends through an opening 380 in the upper lug 340 of the second handle 132, extends through opening 384 in the second link 142, and then extends through an opening 382 in the lower lug 342 of the second handle 132.

Figure 6:
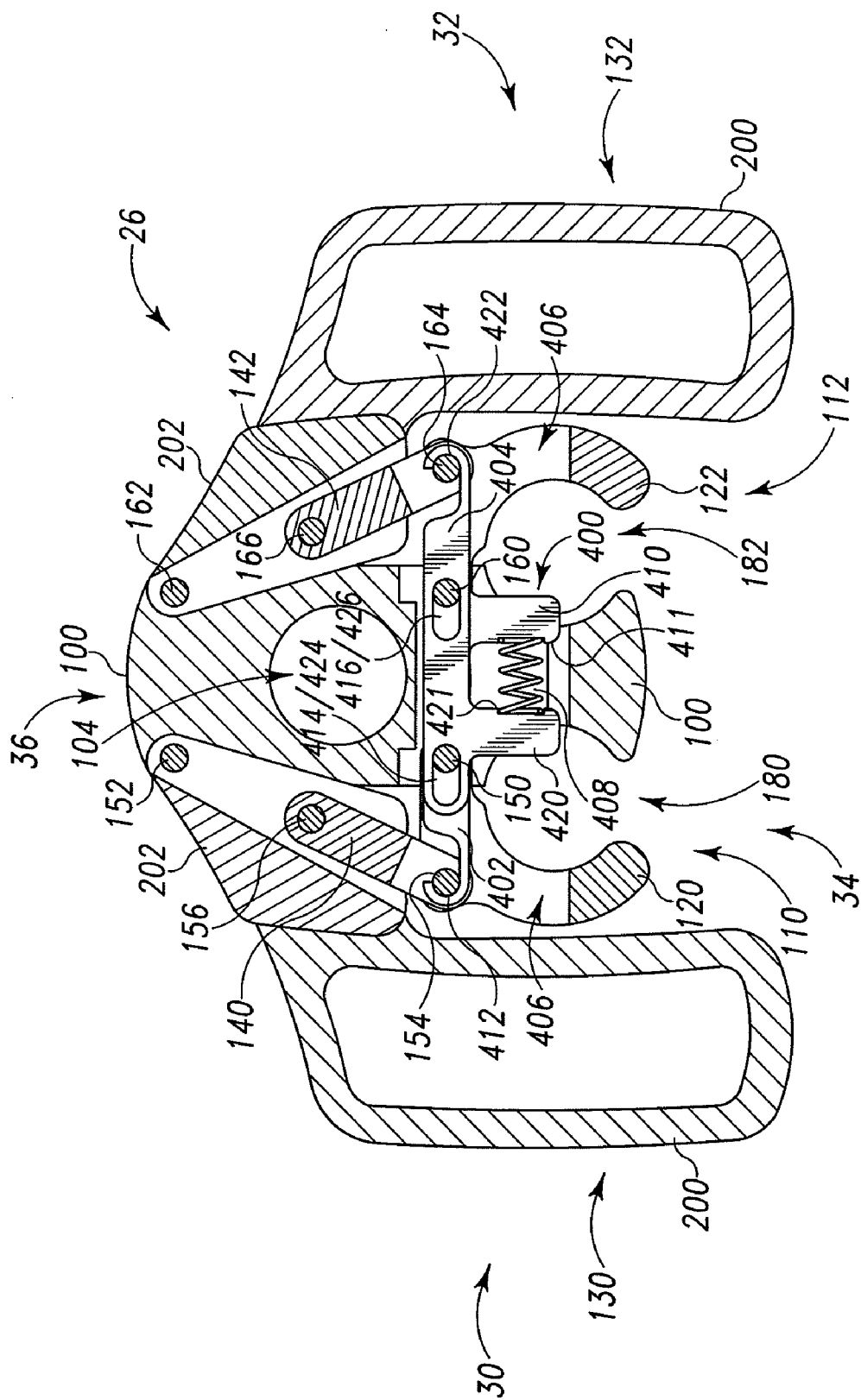
FIG. 6 is a cross sectional view along a line 6-6 in FIG. 2 showing a lock having first and second sliders disposed in their respective retracted latching positions.
Figure 7:
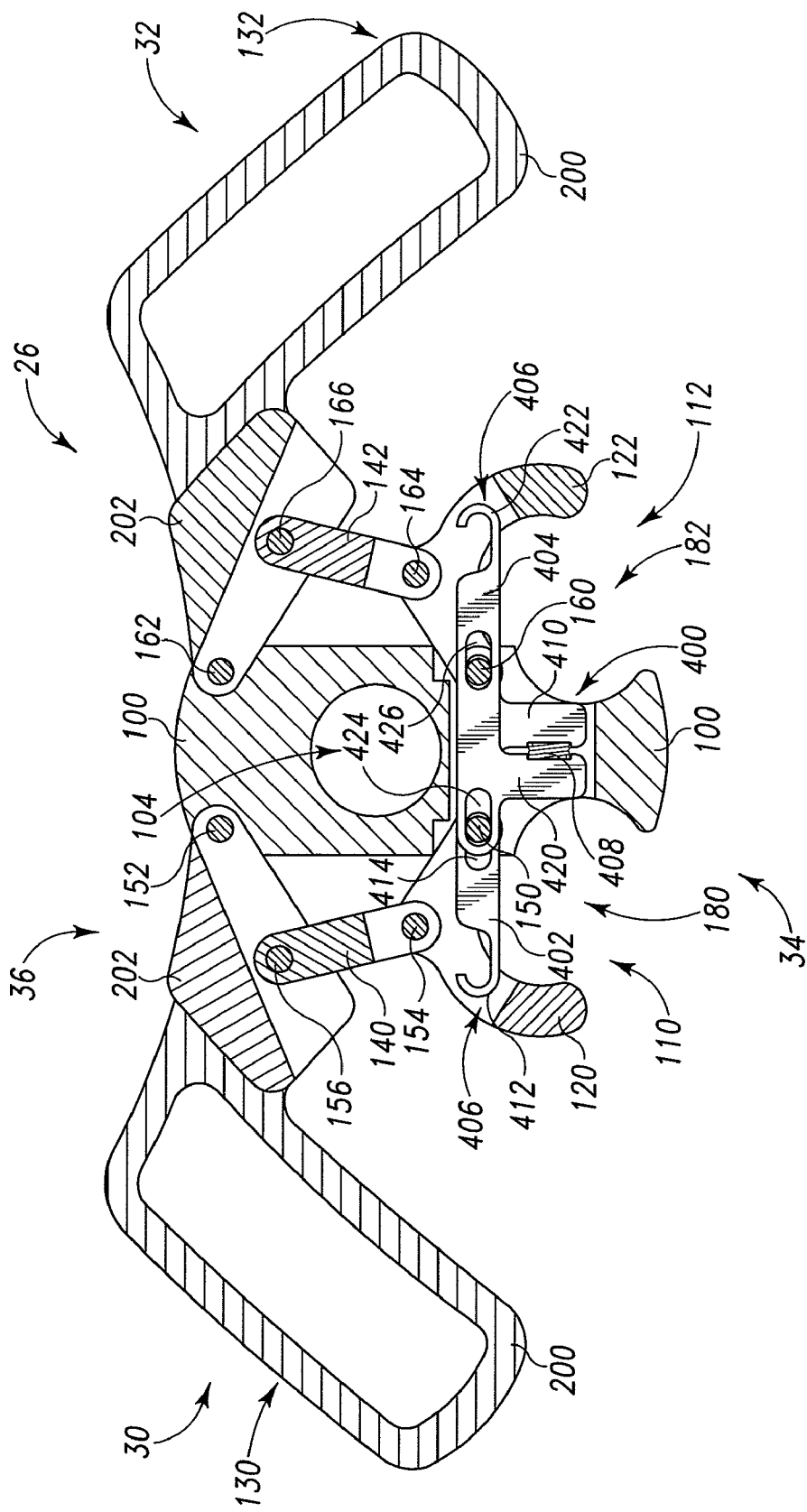
FIG. 7 is a cross sectional view similar to FIG. 6 showing the first and second sliders slider moved to their respective extended unlatching positions.

Referring to FIGS. 6-7, the coupler 26 includes a lock 400 comprising first and second sliders 402, 404. The lock 400 is configured such that in case only one of the three posts 52, 56, 60 is received in any one of the two post-receiving cavities 180, 182 and the associated handle 130, 132 is moved to the closed position, said one of the three posts 52, 56, 60 is locked to the equipment support coupler 26, and such that in case any two of the three posts 52 and 56, or 52 and 60, or 56 and 60 are received in the two post-receiving cavities 180, 182, both of the handles 130, 132 are unlocked so that respective engagements of said two posts 52 and 56, or 52 and 60, or 56 and 60 and the equipment support coupler 26 are releasable.

The first and second sliders 402, 404 are located in a laterally-extending recess 406 (FIGS. 3-4 and 6-7) defined by the spaced-apart lugs 210, 212 on the first side 30 of the mounting block 100, the spaced-apart lugs 310, 312 on the second side 32 of the mounting block 100, the spaced-apart lugs 214, 216 of the first jaw 120, the spaced-apart lugs 314, 316 of the second jaw 122, the spaced-apart lugs 264, 266 of the first link 140, and the spaced-apart lugs 364, 366 of the second link 142. As shown in FIGS. 6-7, the first slider 402 has a first tab 410, a first hook 412, and two laterally-extending slots 414, 416. The second slider 404 has a second tab 420, a second hook 422, and two laterally-extending slots 424, 426. As shown in FIGS. 6-7, the first and fifth pivot pins 150, 160 extend through the slots 414, 416 in the first slider 402 and the slots 424, 426 in the second slider 404 so that the two sliders 402, 404 can move laterally side-to-side. Each slider 402, 402 is movable between a retracted latching position (FIG. 6) and an extended unlatching position (FIG. 7). As shown in FIG. 6, a spring 408 is situated in the recess 406 in the mounting block 100 in a state of compression between inwardly-facing edges 411, 421 of the two tabs 410, 420 of the sliders 402, 404 to bias the sliders 402, 404 toward their respective retracted latching positions as shown in FIG. 6.

As shown in FIG. 6, when the first slider 402 is in its retracted latching position, the first tab 410 of the first slider 402 projects into the second post-receiving cavity 182 and the first hook 412 of the first slider 402 engages the third pivot pin 154 to lock the first handle 130 in its closed position, thereby locking the first jaw 120 in its closed position. As shown in FIG. 6, when the second slider 404 is in its retracted latching position, the second tab 420 of the second slider 404 projects into the first post-receiving cavity 180 and the second hook 422 of the second slider 404 engages the seventh pivot pin 164 to lock the second handle 132 in its closed position, thereby locking the second jaw 122 in its closed position.

As shown in FIG. 7, when the first slider 402 is in its extended unlatching position, the first tab 410 of the first slider 402 is pushed out of the second post-receiving cavity 182 and the first hook 412 of the first slider 402 disengages from the third pivot pin 154 to unlock the first handle 130 to allow it to move between its closed and opened positions. As shown in FIG. 7, when the second slider 404 is in its extended unlatching position, the second tab 420 of the second slider 404 is pushed out of the first post-receiving cavity 180 and the second hook 422 of the second slider 404 disengages from the seventh pivot pin 164 to unlock the second handle 132 to allow it to move between its closed and opened positions.

When the equipment support 20 is carried by the bed 50, the first handle 130 and the first jaw 120 are in their respective closed positions to clamp the first post 52 in the first post-receiving cavity 180. When the first post 52 is received in the first post-receiving cavity 180, the first post 52 pushes the second tab 420 out of the first post-receiving cavity 180 to shift the second slider 404 toward its extended unlatching position, against the bias of the spring 408, to disengage the second hook 422 from engagement with the seventh pivot pin 164 to unlock the second handle 132 to allow it move between its closed and opened positions. The spring 408, however, keeps the first slider 402 in its retracted latching position to lock the first handle 130 in its closed position to prevent a caregiver from inadvertently moving the first handle 130 to its opened position, which may cause the equipment support 20 to fall off the bed 50. Thus, at this point, the first handle 130 is locked and the second handle 132 is unlocked.

Figure 5:
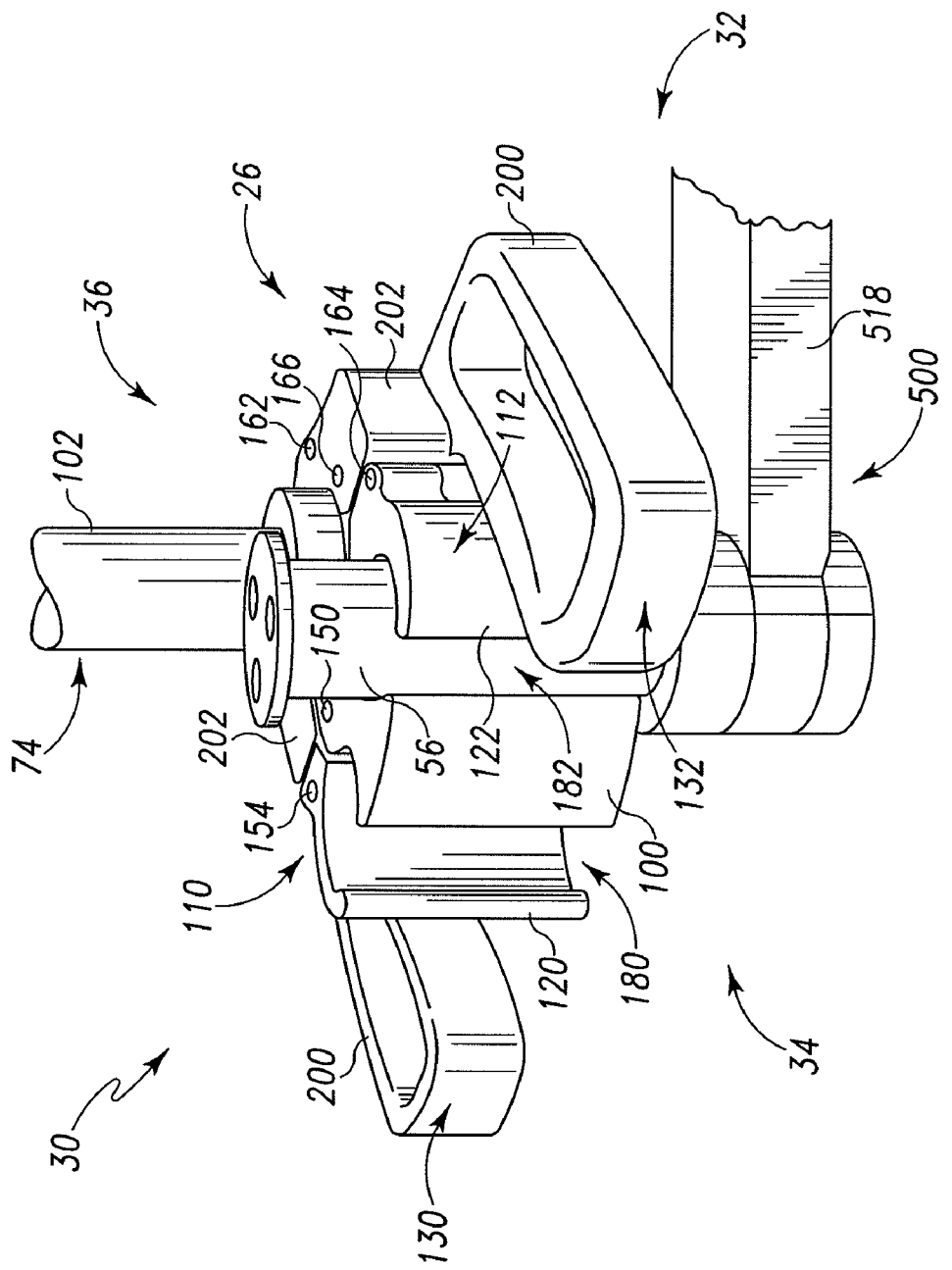
FIG. 5 is an enlarged perspective view similar to FIGS. 3 and 4 showing the upwardly-extending second post of the arm system clamped between the mounting block and the second jaw in response to the second handle moving to the closed position to allow the arm system to carry the equipment support.

To transfer the equipment support 20 from the bed 50 to the arm system 54, the second handle 132, which is unlocked, is moved to its opened position (FIG. 4) to open the second jaw 122 and the second post 56 of the arm system 54 is received in the second post-receiving cavity 182. The second post 56 of the arm system 54 is then clamped between the second jaw 122 and the mounting block 100 by moving the second handle 132, which is unlocked, to its closed position (FIG. 5). When the second post 56 is received in the second post-receiving cavity 182, the second post 56 pushes the first tab 410 out of the second post-receiving cavity 182 to shift the first slider 402 toward its extended unlatching position, against the bias of the spring 408, to disengage the first hook 412 from engagement with the third pivot pin 154 to unlock the first handle 130 to allow it to move between its closed and opened positions. Thus, at this point, both the first and second handles 130, 132 are unlocked.

The first handle 130, which is now unlocked, is then moved to the opened position to open the first jaw 120 to release the first post 52 of the bed 50 to allow the arm system 54 to move away from the bed 50 with the arm system 54 carrying the equipment support 20 (or to allow the bed 50 to move away from the arm system 54 with the arm system 54 carrying the equipment support 20). When the first post 52 of the bed 50 leaves the first post-receiving cavity 180, the spring 408 pushes the second slider 402 back toward its retracted latching position to lock the second handle 132 in its closed position to prevent a caregiver from inadvertently moving the second handle 132 to its opened position, which may cause the equipment support 20 to fall off the arm system 54. The first handle 130, which is unlocked, is then moved to the closed position to close the first jaw 120. Thus, at this point, the first handle 130 is unlocked and the second handle 132 is locked.

To transfer the equipment support 20 from the arm system 54 to the cart 58, the first handle 130, which is unlocked, is moved to the opened position to open the first jaw 120 and the third post 60 of the cart 58 is received in the first post-receiving cavity 180. The third post 60 of the cart 58 is then clamped between the first jaw 120 and the mounting block 100 by moving the first handle 130 to its closed position. When the third post 60 is received in the first post-receiving cavity 180, the third post 60 pushes the second tab 410 out of the first post-receiving cavity 180 to shift the second slider 404 toward its extended unlatching position, against the bias of the spring 408, to disengage the second hook 422 from engagement with the seventh pivot pin 164 to unlock the second handle 132 to allow it to move between its closed and opened positions. Thus, at this point, both the first and second handles 130, 132 are unlocked.

The second handle 132, which is unlocked, is then moved to the opened position to open the second jaw 122 to release the second post 56 of the arm system 54 to allow the cart 58 to move away from the arm system 54 with the cart 58 carrying the equipment support 20 (or to allow the arm system 54 to move away from the cart 58 with the cart 58 carrying the equipment support 20). When the second post 56 of the arm system 54 leaves the second post-receiving cavity 182, the spring 408 pushes the first slider 402 back toward its retracted latching position to lock the first handle 130 in its closed position to prevent a caregiver from inadvertently moving the first handle 130 to its opened position, which may cause the equipment support 20 to fall off the cart 58. The second handle 132, which is unlocked, is then moved to the closed position to close the second jaw 122. Thus, at this point, the first handle 130 is locked and the second handle 132 is unlocked.

To transfer the equipment support 20 from the cart 58 to the bed 50, the second handle 132, which is unlocked, is moved to the releasing position to open the second jaw 122 and the first post 52 of the bed 50 is received in the second post-receiving cavity 182. The first post 52 of the bed 50 is then clamped between the second jaw 122 and the mounting block 100 by moving the second handle 132 to its closed position. When the first post 52 is received in the second post-receiving cavity 182, the first post 52 pushes the first tab 410 out of the second post-receiving cavity 182 to shift the first slider 402 toward its extended unlatching position, against the bias of the spring 408, to disengage the first hook 412 from engagement with the third pivot pin 154 to unlock the first handle 130 to allow it to move between its closed and opened positions. Thus, at this point, both the first and second handles 130, 132 are unlocked.

The first handle 130, which is now unlocked, is then moved to the releasing position to open the first jaw 120 to release the third post 60 of the cart 58 to allow the cart 58 to move away from the bed 50 with the bed 50 carrying the equipment support 20 (or to allow the bed 50 to move away from the cart 58 with the bed 50 carrying the equipment support 20). When the third post 60 of the cart 58 leaves the first post-receiving cavity 180, the spring 408 pushes the second slider 402 back toward its retracted latching position to lock the second handle 132 in its closed position to prevent a caregiver from inadvertently moving the second handle 132 to its opened position, which may cause the equipment support 20 to fall off the bed 50. The first handle 130, which is unlocked, is then moved to the closed position to close the first jaw 120. At this point, the first handle 130 is unlocked and the second handle 132 is locked. Thus, the equipment support 20 is directly transferable from the bed 50 to the arm system 54 to the cart 58 and back to the bed 50, in any order.

As shown in FIG. 8, a bed mount 450 includes a mounting bracket 452 that is coupled to a corner bracket 866 (FIG. 16) of the hospital bed 50 by suitable fasteners, such as, for example, nut and bolt combinations 454. An arm 456 has a proximal end 458 coupled to the mounting bracket 452 for pivoting movement about a first pivot axis 460. The upwardly-extending first post 52 is coupled to a distal end 462 of the arm 456 for pivoting movement about a second pivot axis 464.

Figure 9:
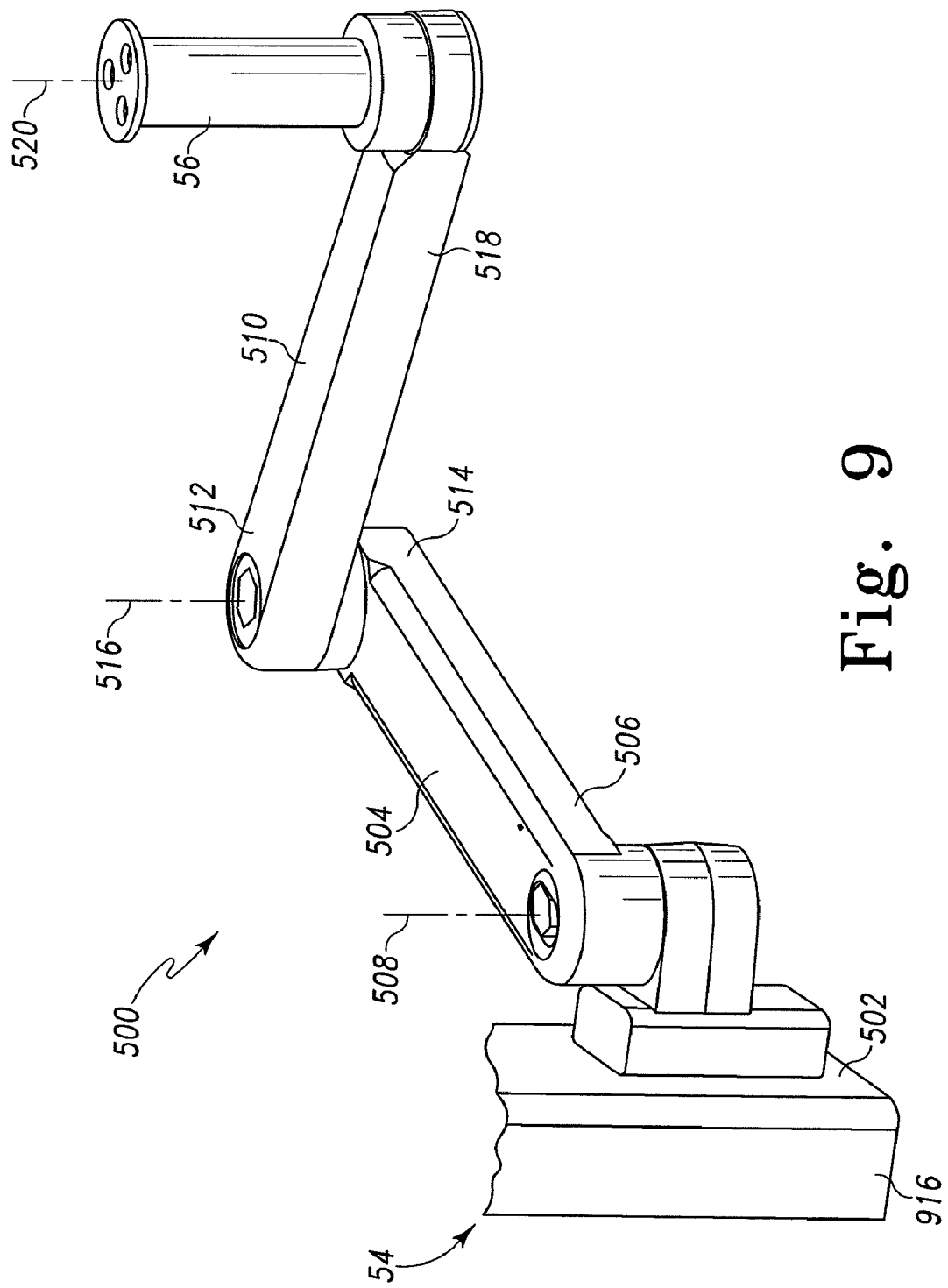
FIG. 9 is a perspective view, similar to FIG. 8, of an arm mount showing the arm mount including a mounting bracket coupled to an accessory rail of a service head extending downwardly from a telescoping radial arm of the arm system, a first arm having a proximal end coupled to the mounting bracket for pivoting movement about a first pivot axis, a second arm having a proximal end coupled to a distal end of the first arm for pivoting movement about a second pivot axis, and the upwardly-extending post coupled to a distal end of the second arm for pivoting movement about a third pivot axis.

As shown in FIG. 9, an arm mount 500 includes a mounting bracket 502 coupled to a service head 916 (FIG. 20) extending downwardly from a radial arm 908 of the arm system 54. A first arm 504 has a proximal end 506 coupled to the mounting bracket 502 for pivoting movement about a first pivot axis 508. A second arm 510 has a proximal end 512 coupled to a distal end 514 of the first arm 504 for pivoting movement about a second pivot axis 516. The upwardly-extending post 56 is coupled to a distal end 518 of the second arm 510 for pivoting movement about a third pivot axis 520.

Figure 10:
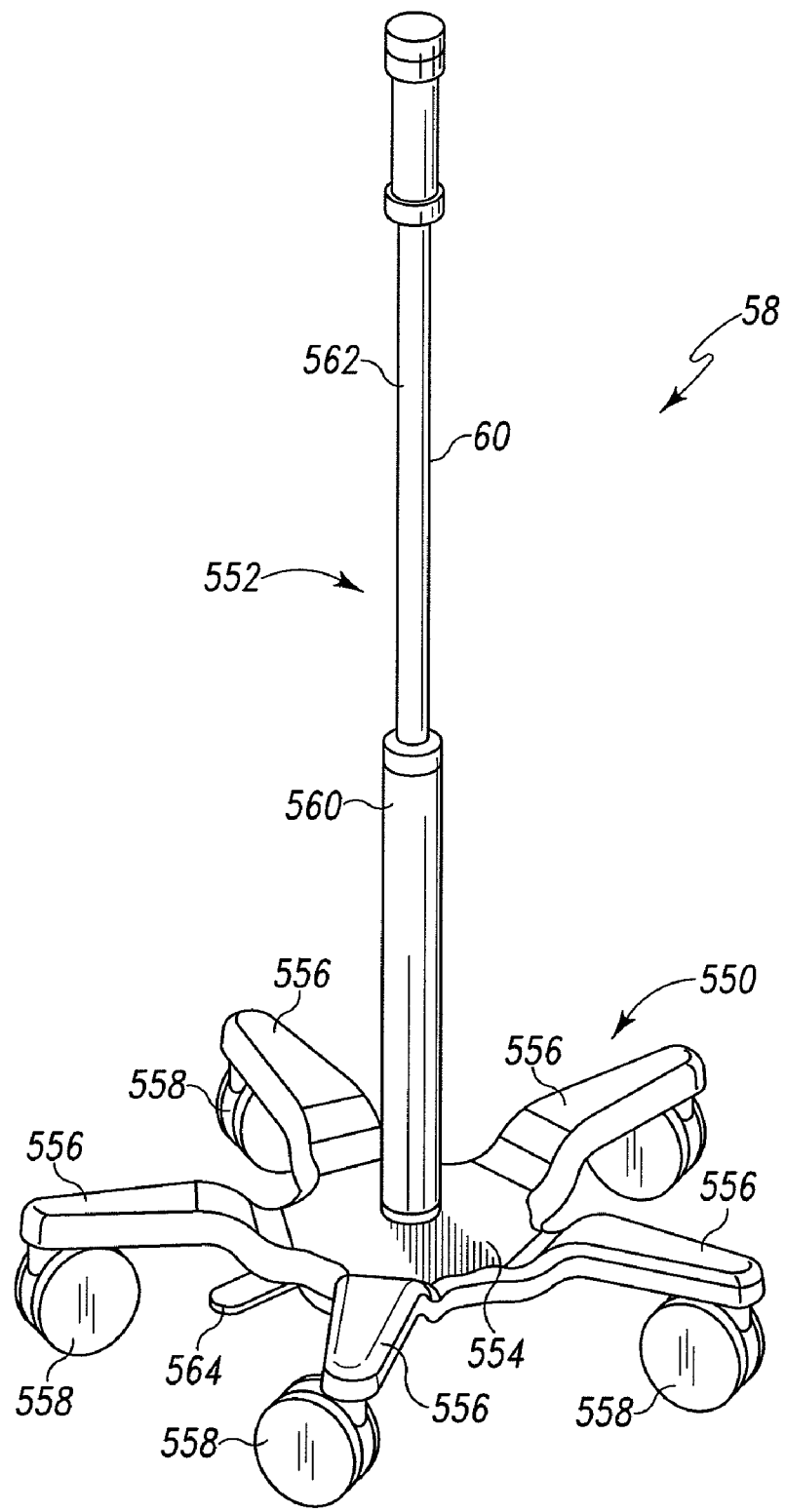
FIG. 10 is a perspective view of a cart showing the cart including a base supported on wheels and a telescoping column extending upwardly from the base.
Figure 11:
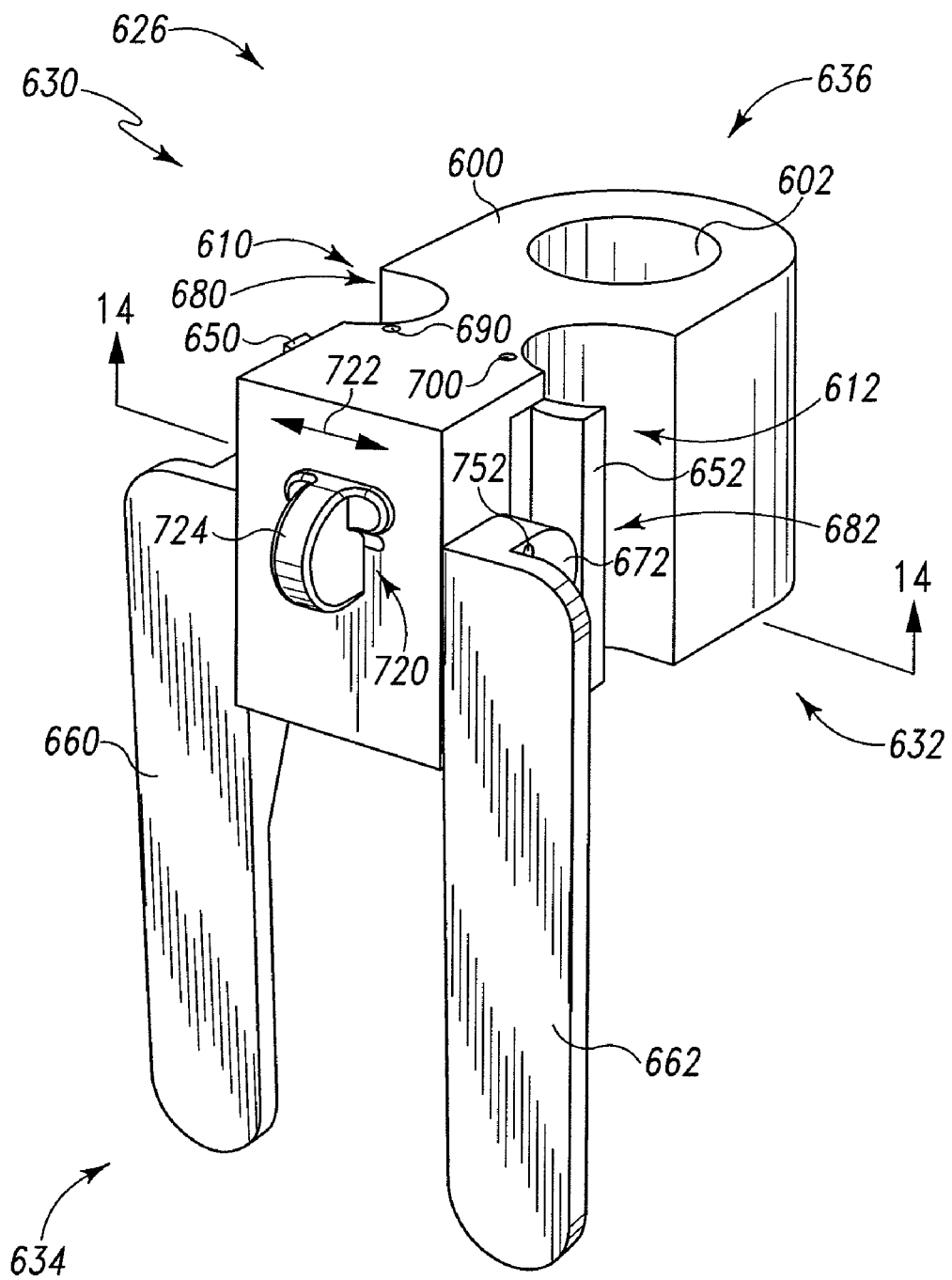
FIG. 11 is a perspective view of a second embodiment of the coupler shown in FIGS. 1-7 showing a mounting block configured to be coupled to an equipment supporting portion, a first clamp having a first jaw and a first handle coupled to a first side of the mounting block, a second clamp having a second jaw and a second handle coupled to a second side of the mounting block, a latch coupled to a front side of the mounting block for side-to-side movement, the first jaw moving between a closed position and an opened position as the first handle moves between a closed position and an opened position, the second jaw moving between a closed position and an opened position as the second handle moves between a closed position and an opened position, the first jaw, the first handle, the second jaw, and the second handle being shown in their respective closed positions.

As shown in FIG. 10, a cart 58 includes a wheeled base 550 and a telescoping column 552 extending upwardly from the base 550. The base 550 has a central hub 554 and five spokes 556 radiating substantially horizontally outwardly from the central hub 554. Casters 558 are coupled to distal ends of the spokes 556. In the illustrated embodiment, the column 552 includes an outer tube 560 extending upwardly from the central hub 554 and an inner tube 562 that telescopes into and out of the outer tube 560. The inner tube 562 comprises the third upwardly-extending post 60 of the cart 58. In the illustrated embodiment, a manually operable locking mechanism, such as a gas spring (not shown), is located inside the outer tube 560 to releasably secure the inner tube 562 in a selected vertical position relative to the outer tube 560. A release pedal 564 extends outwardly from the base 550 and is operable to unlock the gas spring. Bearings (not shown) may be provided to facilitate telescoping movement of the inner tube 562 relative to the outer tube 560.

FIGS. 11-15 show a second embodiment 626 of the coupler 26 shown in FIGS. 1-7. The coupler 626 includes a mounting block 600 that, in the illustrated embodiment, has a bore 602 in which the lower portion 102 of the central post 74 is received for pivoting movement about the pivot axis 106 to allow the equipment supporting portion 22 to rotate relative to the mounting block 600 for improved access. The coupler 626 further includes first and second clamps 610, 612 coupled to the mounting block 600 on first and second sides 630, 632 thereof. As shown in FIGS. 11-15, the first clamp 610 includes a first jaw 650 and a first handle 660 coupled to the first side 630 of the mounting block 600 and a first cam 670 coupled to the first handle 660 and coupled to the first jaw 650. The second clamp 612 includes a second jaw 652 and a second handle 662 coupled to the second side 632 of the mounting block 600 and a second cam 672 coupled to the second handle 662 and coupled to the second jaw 652. In the illustrated embodiment, each cam 670, 672 is integrally formed with the associated handle 660, 662 (as shown, for example, in FIG. 15 with respect to the first cam 670 and the first handle 660).

Figure 12:
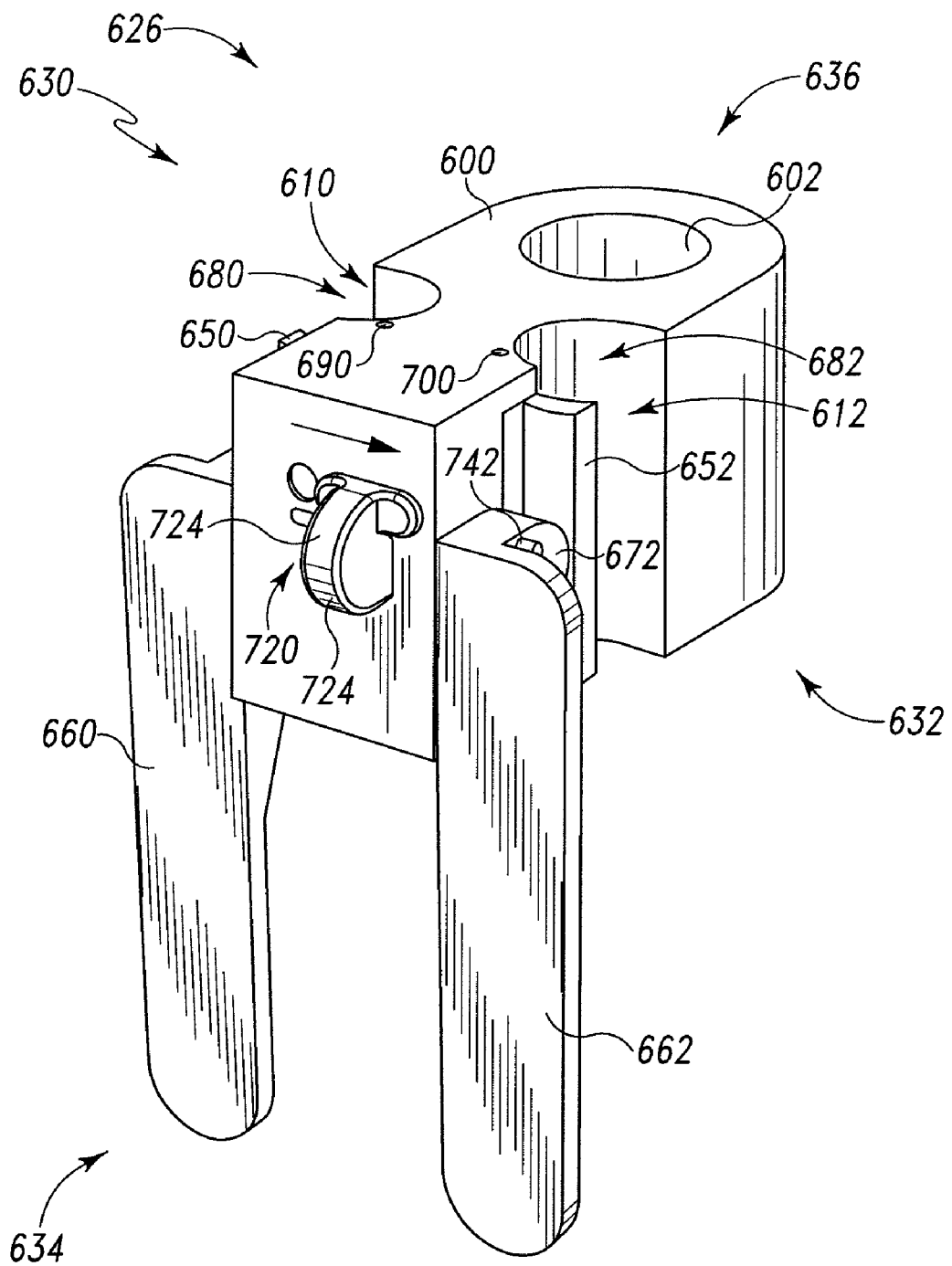
FIG. 12 is a perspective view similar to FIG. 11 showing the latch moved to the second side of the mounting block to lock the second handle in its closed position and to unlock the first handle to allow it to move between its closed and opened positions.
Figure 13:
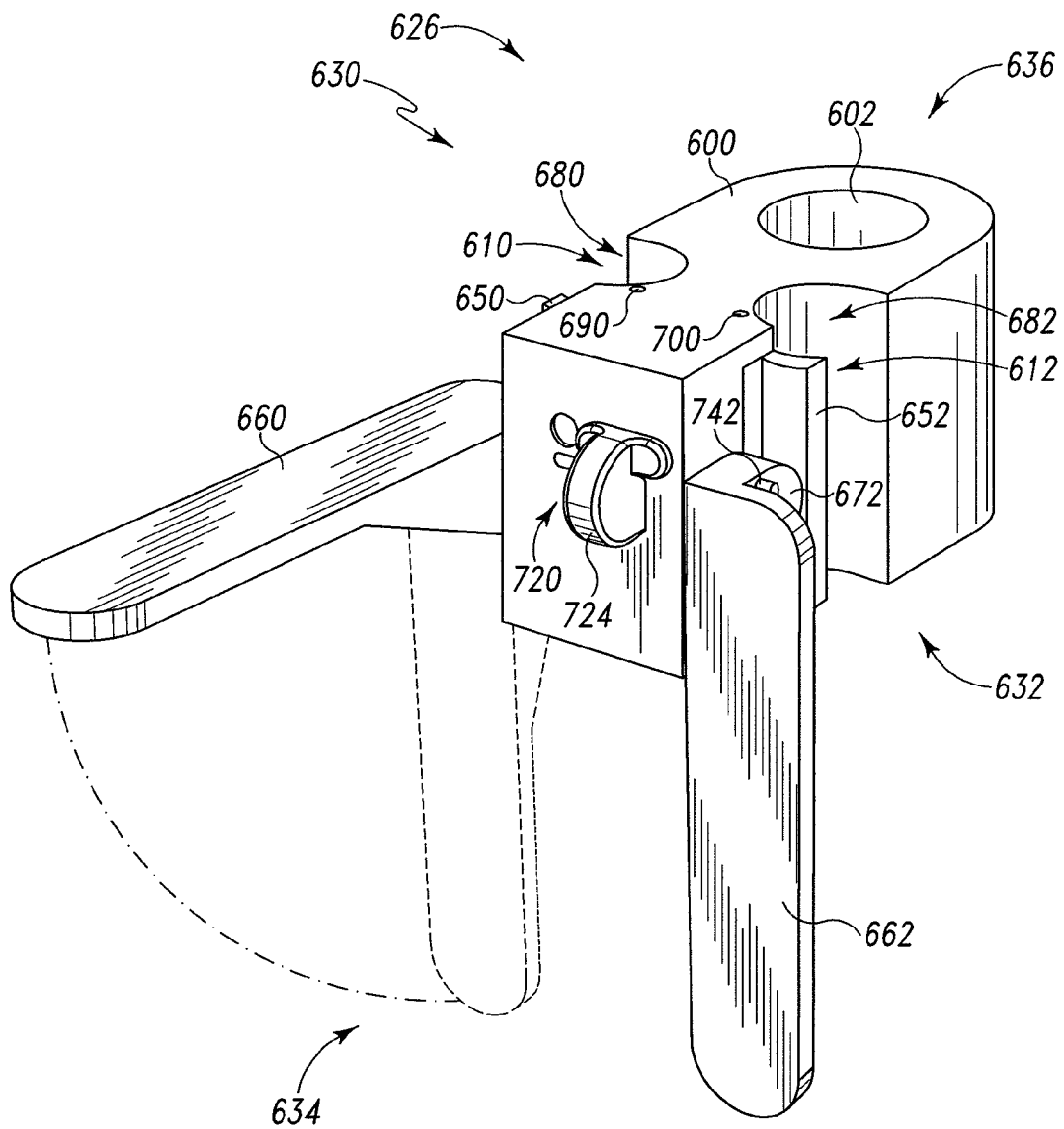
FIG. 13 is a perspective view similar to FIG. 12 showing the first jaw moving to its opened position in response to the first handle moving to its opened position.

The first jaw 650 moves between a closed position (FIGS. 11-12) and an opened position (FIG. 13) as the first handle 660 moves between a closed position (FIGS. 11-12) and an opened position (FIG. 13). The second jaw 652 moves between a closed position (FIGS. 11-12) and an opened position (shown in FIG. 13 with respect to the first jaw 650) as the second handle 662 moves between a closed position (FIGS. 11-12) and an opened position (shown in FIG. 13 with respect to the first handle 660). The first jaw 650 and the first side 630 of the mounting block 600 define a first post-receiving cavity 680. The second jaw 652 and the second side 632 of the mounting block 600 define a second post-receiving cavity 682.

In the illustrated embodiment, like the clamps 110, 112 of the coupler 26, the two clamps 610, 612 are generally mirror images of each other. Each post-receiving cavity 680, 682 is configured to receive any of the three posts 52, 56, 60 of the bed 50, the arm system 54 and the cart 58, respectively. Thus, the first post 52 of the bed 50 may be clamped in the first post-receiving cavity 680 or the second post-receiving cavity 682. Likewise, the second post 56 of the arm system 54 may be clamped in the first post-receiving cavity 680 or the second post-receiving cavity 682 and the third post 60 of the cart 58 may be clamped in the first post-receiving cavity 680 or the second post-receiving cavity 682. The operation of the coupler 626 is generally similar to the operation of the coupler 26.

The first jaw 650 is coupled to the first side 630 of the mounting block 600 for pivoting movement about a generally vertically-extending first pivot pin 690. The first handle 660 is coupled to the first side 630 of the mounting block 600 for pivoting movement about a generally horizontally-extending second pivot pin 692. The second jaw 652 is coupled to the second side 632 of the mounting block 600 for pivoting movement about a generally vertically-extending first pivot pin 700. The second handle 662 is coupled to the second side 632 of the mounting block 600 for pivoting movement about a generally horizontally-extending second pivot pin 702. In some embodiments, the ends of the pivot pins 690, 692, 700, 702 have circumferential grooves for receiving respective C-washers (not shown) to retain the pivot pins 690, 692, 700, 702 in place.

The first and second jaws 650, 652 are spring biased toward their respective opened positions with a compression spring (not shown) to bias contoured outer surfaces 710 (FIG. 15) of the first and second jaws 650, 652 in engagement with contoured outer surfaces 712 (FIG. 15) of the first and second cams 670, 672. As each handle 660, 662 is rotated approximately 90 degrees in a direction 714 (FIG. 15) from its opened position (shown in FIG. 13 with respect to the first handle 660) to its closed position (FIGS. 11-12), the rearwardly-facing contoured outer surface 712 of the associated cam 670, 672 presses against the forwardly-facing contoured outer surface 710 of the associated jaw 650, 652 to move the associated jaw 650, 652 toward its closed position. Rotation of said handle 660, 662 approximately 90 degrees in an opposite direction 716 (FIG. 15) rotates the associated cam 670, 672 therewith and the biasing spring causes the associated jaw 650, 652 to move from its closed position to its opened position. Thus, each jaw 650, 652 moves between a closed position (FIGS. 11-12) and an opened position (shown in FIG. 13 with respect to the first jaw 650) as the associated handle 660, 662 moves between a closed position (FIGS. 11-12) and an opened position (shown in FIG. 13 with respect to the first handle 660).

Figure 14:
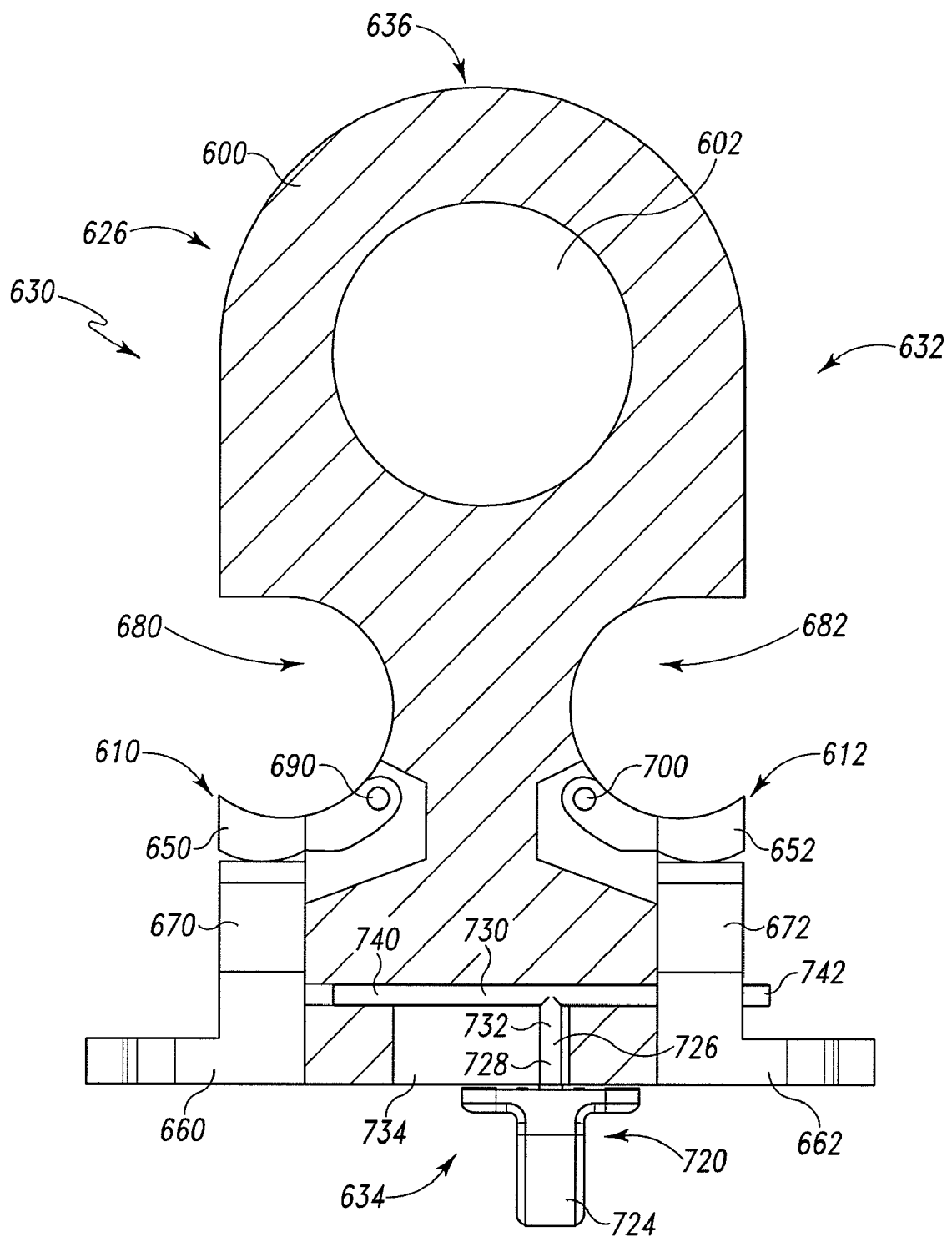
FIG. 14 is a cross sectional view along a line 14-14 in FIG. 11 showing a locking pin that is retracted from an opening in the first handle to unlock the first handle to allow it to move between its closed and opened positions and that is extended into an opening in the second handle to lock the second handle in its closed position in response to the latch moving to the second side of the mounting block.
Figure 15:
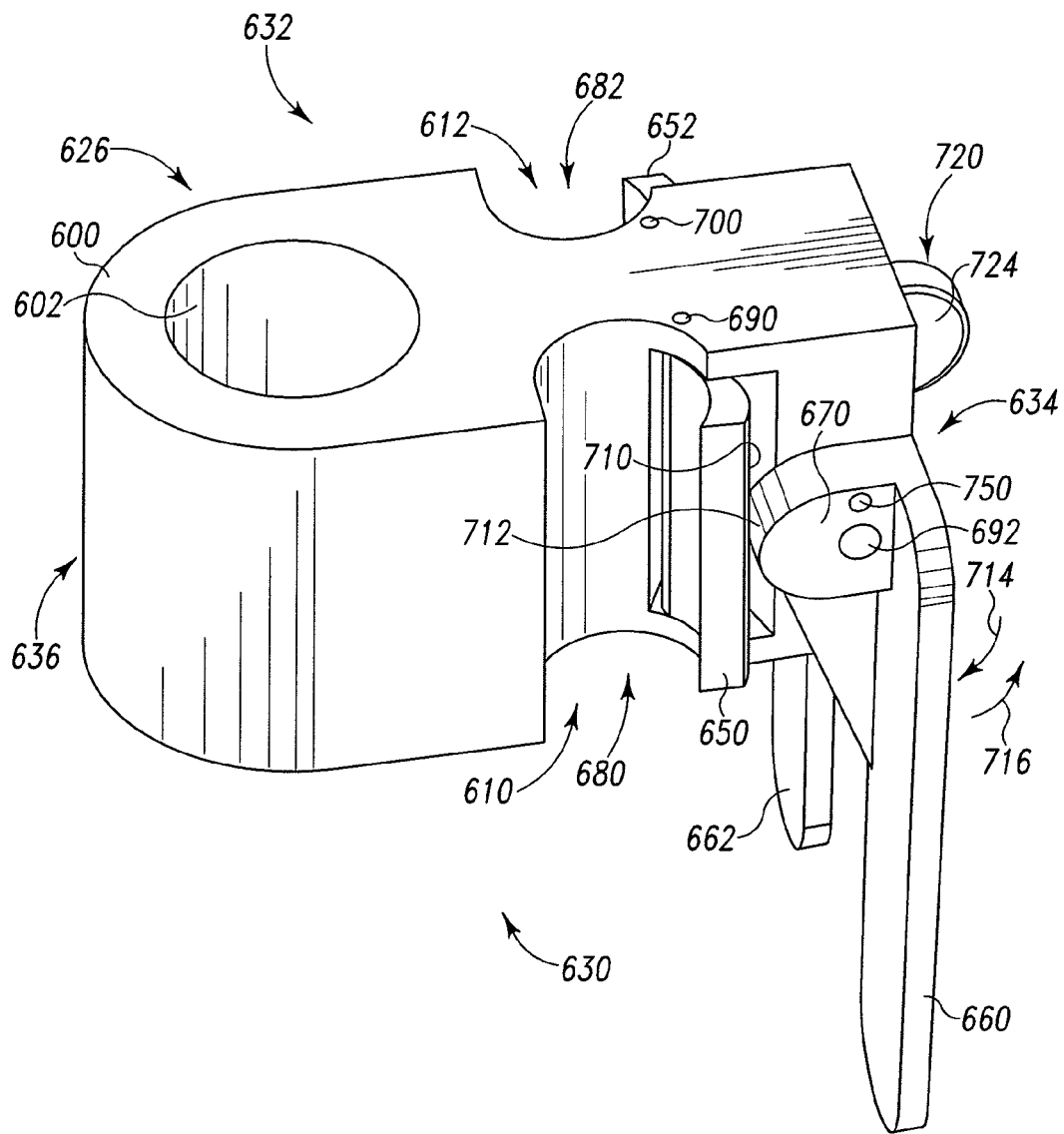
FIG. 15 is a perspective view of the coupler of FIGS. 11-14 showing a first post-receiving cavity defined by the first jaw and the mounting block.

As shown in FIGS. 11-15, the coupler 626 includes a latch 720 coupled to a front side 634 of the mounting block 600 for side-to-side lateral movement as indicated by a double-headed arrow 722. As shown in FIG. 14, the latch 720 comprises a finger grip 724, a connecting link 726 that extends rearwardly from the finger grip 724 and that has a proximal end 728 coupled to the finger grip 724 and a laterally-extending locking pin 730 (FIG. 14) coupled to a distal end 732 of the connecting link 726. The connecting link 726 is located in a longitudinally-extending slot 734 in the mounting block 600. The locking pin 730 is located in a laterally-extending slot 736 in the mounting block 600. The longitudinally-extending slot 734 opens at a front surface of the mounting block 600 and opens into the laterally-extending slot 736. The laterally-extending slot 736 opens at side surfaces of the mounting block 600.

When the finger grip 724 is centered with respect to the mounting block 600 and both handles 660, 662 are in their respective closed positions, a first portion 740 of the locking pin 730 on the first side 630 of the mounting block 600 is received in a first opening 750 (FIG. 15) in the first handle 660 to lock the first handle 660 in its closed position and a second portion 742 of the locking pin 730 on the second side 632 of the mounting block 600 is received in a second opening 752 in the second handle 662 to lock the second handle 662 in its closed position.

When the finger grip 724 is moved to the first side 630 while the first handle 660 is in its closed position, the first portion 740 (FIG. 14) of the locking pin 730 extends further into the first opening 750 (FIG. 15) in the first handle 660 to keep the first handle 660 locked in its closed position and the second portion 742 (FIG. 14) of the locking pin 730 is retracted completely out of the second opening 752 (FIG. 11) in the second handle 662 to unlock the second handle 662 to allow it to move between its closed and opened positions. Likewise, when the finger grip 724 is moved to the second side 632 while the second handle 662 is in its closed position as shown in FIG. 12-14, the second portion 742 (FIG. 14) of the locking pin 730 extends further into the second opening 752 (FIG. 11) in the second handle 662 to keep the second handle 662 locked in its closed position and the first portion 740 (FIG. 14) of the locking pin 730 is retracted completely out of the first opening 750 (FIG. 15) in the first handle 660 to unlock the first handle 660 to allow it to move between its closed and opened positions.

Thus, the latch 720 is movable to the first side 630 when the first handle 660 is in its closed position to lock the first jaw 650 and the first handle 660 in their respective closed positions and to unlock the second handle 662 to allow it to move between its closed and opened positions. Likewise, the latch 720 is movable to the second side 632 when the second handle 662 is in its closed position to lock the second jaw 652 and the second handle 662 in their respective closed positions and to unlock the first handle 660 to allow it to move between its closed and opened positions. However, the latch 720 is not be movable to the first side 630 when the first handle 630 is in the opened position and the latch 720 is not be movable to the second side 632 when the second handle 662 is in the opened position. This is because the openings 750, 752 (shown in FIGS. 15 and 11, respectively) are aligned with the locking pin 730 only when the handles 660, 662 are in their respective closed positions.

The operation of the coupler 626 is generally similar to the operation of the coupler 26. For the purposes of the following description, it will be assumed that the coupler 626, instead of the coupler 26 shown in FIGS. 1-8, is coupled to the lower portion 102 of the central post 74 of the equipment support 20. When the equipment support 20 is carried by the bed 50, the first handle 660 and the first jaw 650 are in their respective closed positions to clamp the first post 52 in the first post-receiving cavity 680. The latch 720 is then moved to the first side 630 to lock the first jaw 650 and the first handle 660 in their respective closed positions to prevent a caregiver from inadvertently moving the first handle 660 to its opened position, which may cause the equipment support 20 to fall off the bed 50. When the latch 720 moves to the first side 630, the second handle 662 is unlocked. Thus, at this point, the first handle 660 is locked and the second handle 662 is unlocked.

To transfer the equipment support 20 from the bed 50 to the arm system 54, the second handle 132, which is unlocked, is moved to its opened position to open the second jaw 652 and the second post 56 of the arm system 54 is received in the second post-receiving cavity 682. The second post 56 of the arm system 54 is then clamped between the second jaw 652 and the mounting block 600 by moving the second handle 662, which is unlocked, to its closed position. The latch 720 is then moved to the second side 632 to lock the second jaw 652 and the second handle 662 in their respective closed positions to prevent a caregiver from inadvertently moving the second handle 662 to its opened position, which may cause the equipment support 20 to fall off the arm system 54. When the latch 720 moves to the second side 632, the first handle 660 is unlocked. Thus, at this point, the first handle 660 is unlocked and the second handle 662 is locked.

The first handle 660, which is now unlocked, is then moved to the opened position to open the first jaw 650 to release the first post 52 of the bed 50 to allow the arm system 54 to move away from the bed 50 with the arm system 54 carrying the equipment support 20 (or to allow the bed 50 to move away from the arm system 54 with the arm system 54 carrying the equipment support 20). The first handle 660, which is unlocked, is then moved to the closed position to close the first jaw 650. At this point, the first handle 660 is unlocked and the second handle 662 is locked.

To transfer the equipment support 20 from the arm system 54 to the cart 58, the first handle 130, which is unlocked, is moved to the opened position to open the first jaw 650 and the third post 60 of the cart 58 is received in the first post-receiving cavity 680. The third post 60 of the cart 58 is then clamped between the first jaw 650 and the mounting block 600 by moving the first handle 660 to its closed position. The latch 720 is then moved to the first side 630 to lock the first jaw 650 and the first handle 660 in their respective closed positions to prevent a caregiver from inadvertently moving the first handle 660 to its opened position, which may cause the equipment support 20 to fall off the cart 58. When the latch 720 moves to the first side 630, the second handle 662 is unlocked. Thus, at this point, the first handle 660 is locked and the second handle 662 is unlocked.

The second handle 662, which is unlocked, is then moved to the opened position to open the second jaw 652 to release the second post 56 of the arm system 54 to allow the cart 58 to move away from the arm system 54 with the cart 58 carrying the equipment support 20 (or to allow the arm system 54 to move away from the cart 58 with the cart 58 carrying the equipment support 20). The second handle 662, which is unlocked, is then moved to the closed position to close the second jaw 652. Thus, at this point, the first handle 660 is locked and the second handle 662 is unlocked.

To transfer the equipment support 20 from the cart 58 to the bed 50, the second handle 662, which is unlocked, is moved to the releasing position to open the second jaw 652 and the first post 52 of the bed 50 is received in the second post-receiving cavity 682. The first post 52 of the bed 50 is then clamped between the second jaw 652 and the mounting block 600 by moving the second handle 662 to its closed position. The latch 720 is then moved to the second side 632 to lock the second jaw 652 and the second handle 662 in their respective closed positions to prevent a caregiver from inadvertently moving the second handle 662 to its opened position, which may cause the equipment support 20 to fall off the bed 50. When the latch 720 moves to the second side 632, the first handle 660 is unlocked. Thus, at this point, the first handle 660 is unlocked and the second handle 662 is locked.

The first handle 660, which is now unlocked, is then moved to the releasing position to open the first jaw 650 to release the third post 60 of the cart 58 to allow the cart 58 to move away from the bed 50 with the bed 50 carrying the equipment support 20 (or to allow the bed 50 to move away from the cart 58 with the bed 50 carrying the equipment support 20). The first handle 660, which is unlocked, is then moved to the closed position to close the first jaw 650. At this point, the first handle 660 is unlocked and the second handle 662 is locked. Thus, the equipment support 20 is directly transferable from the bed 50 to the arm system 54 to the cart 58 and back to the bed 50, in any order.

Figure 16:
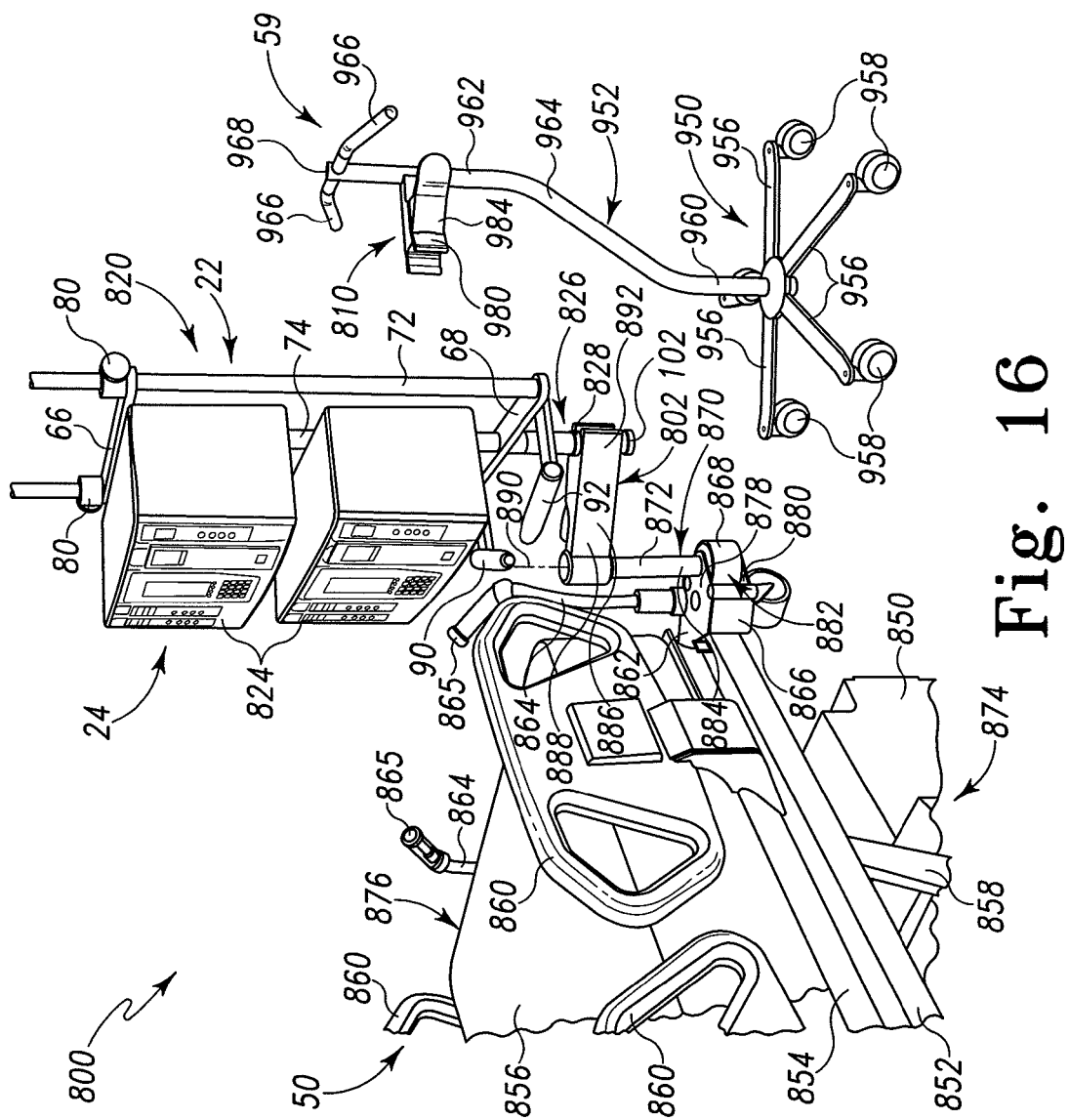
FIG. 16 is a perspective view a patient care equipment management system comprising an equipment support that can be transferred from a hospital bed having a first clamp to an arm system having a second clamp to a wheeled cart having a third clamp, and showing the first clamp of the hospital bed clamping a downwardly-extending post of the equipment support and further showing the wheeled cart having the third clamp positioned next to the hospital bed.
Figure 17:
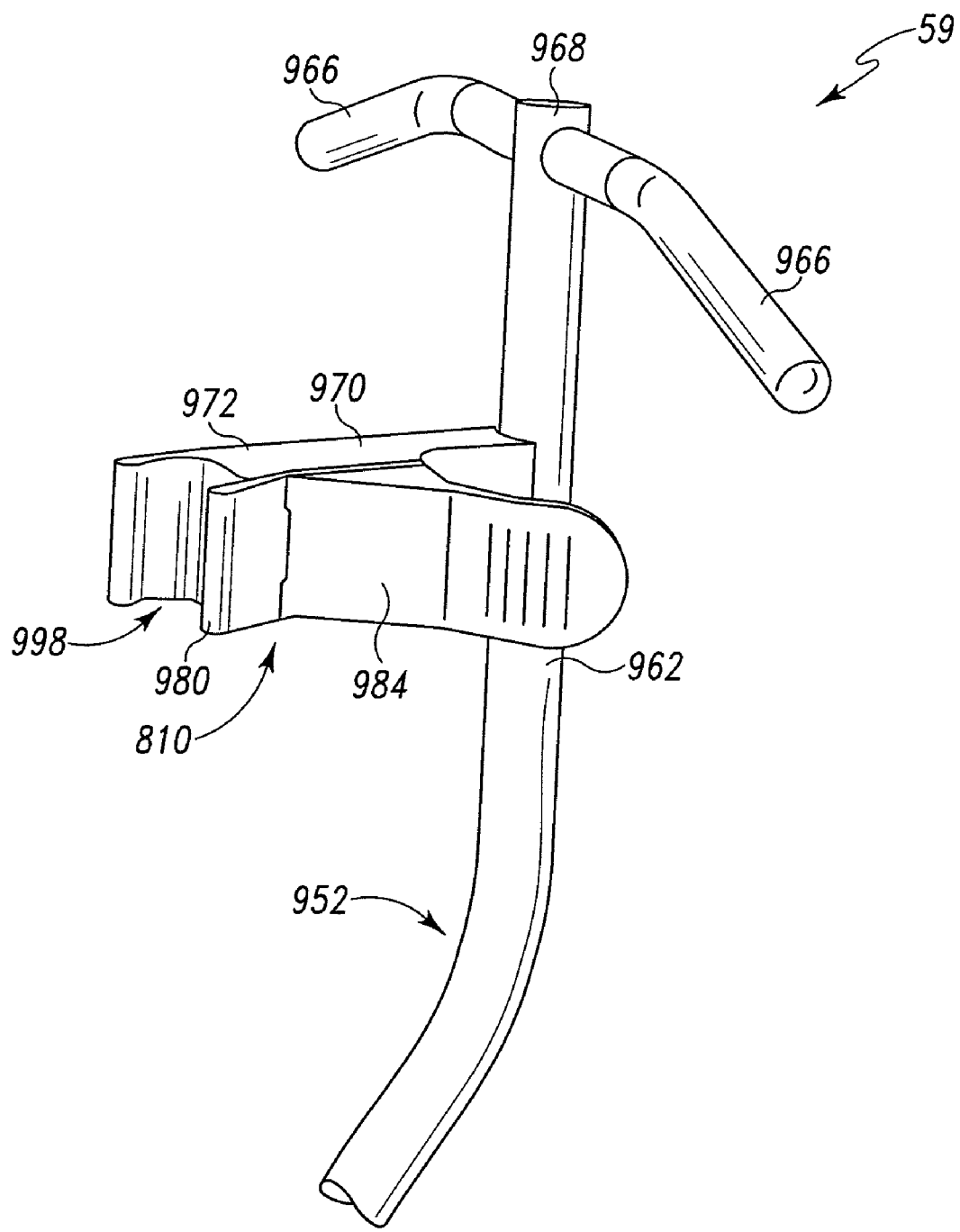
FIG. 17 is an enlarged perspective view of the third clamp of the cart showing a movable jaw of the third clamp moved to an opened position in response to a handle moving to an opened position.
Figure 18:
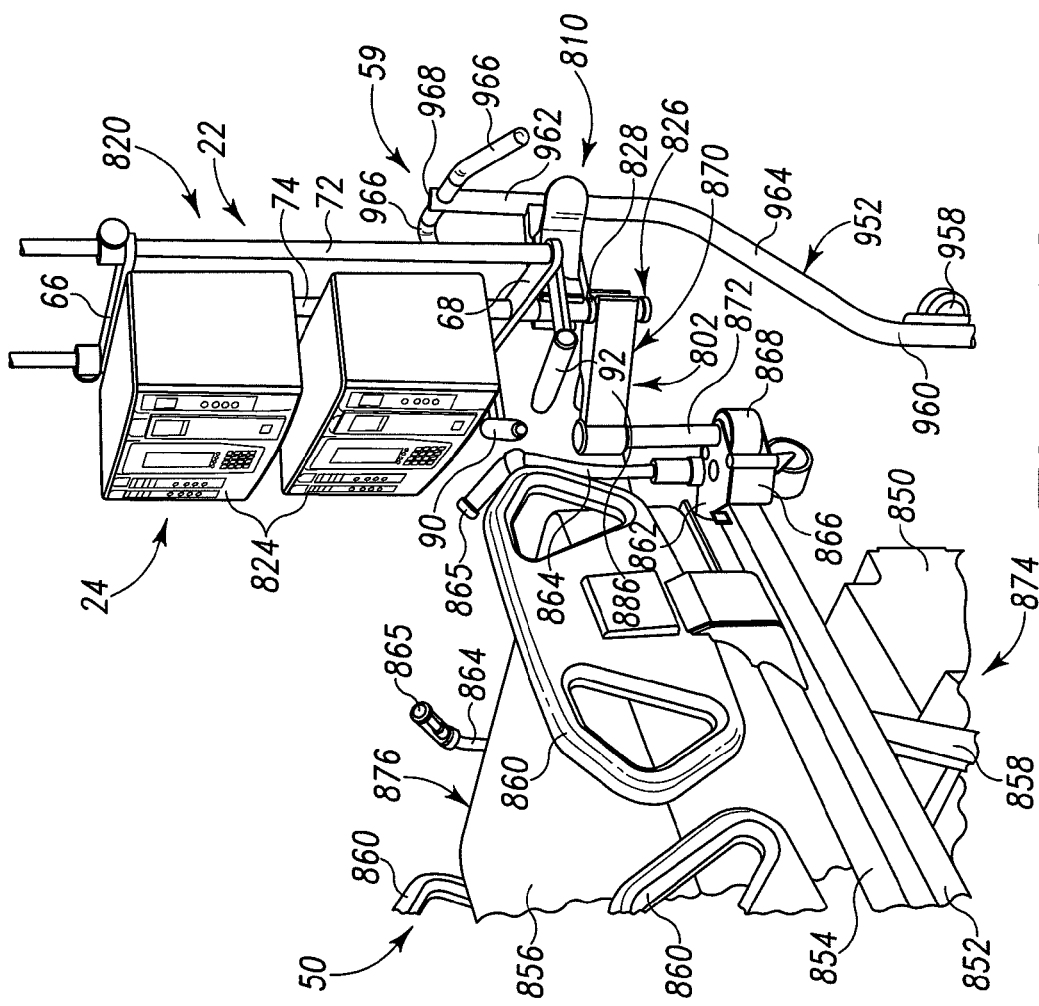
FIG. 18 is a perspective view similar to FIG. 16 showing the downwardly-extending post of the equipment support received in a post-receiving cavity defined by the movable jaw of the third clamp of the cart.
Figure 19:
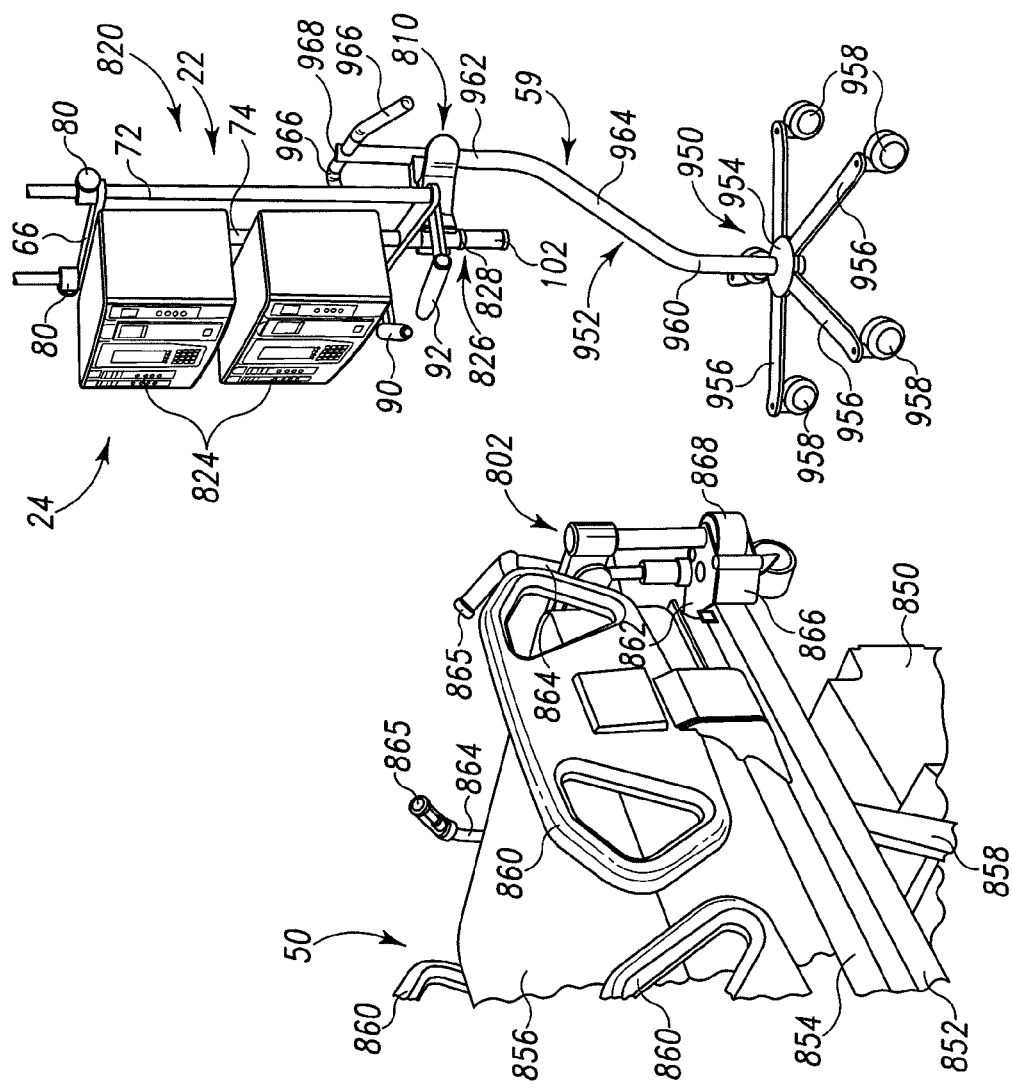
FIG. 19 is a perspective view similar to FIG. 18 showing the third clamp of the wheeled cart clamping the downwardly-extending post of the equipment support and showing the cart moving away from the bed with the cart carrying the equipment support.
Figure 20:
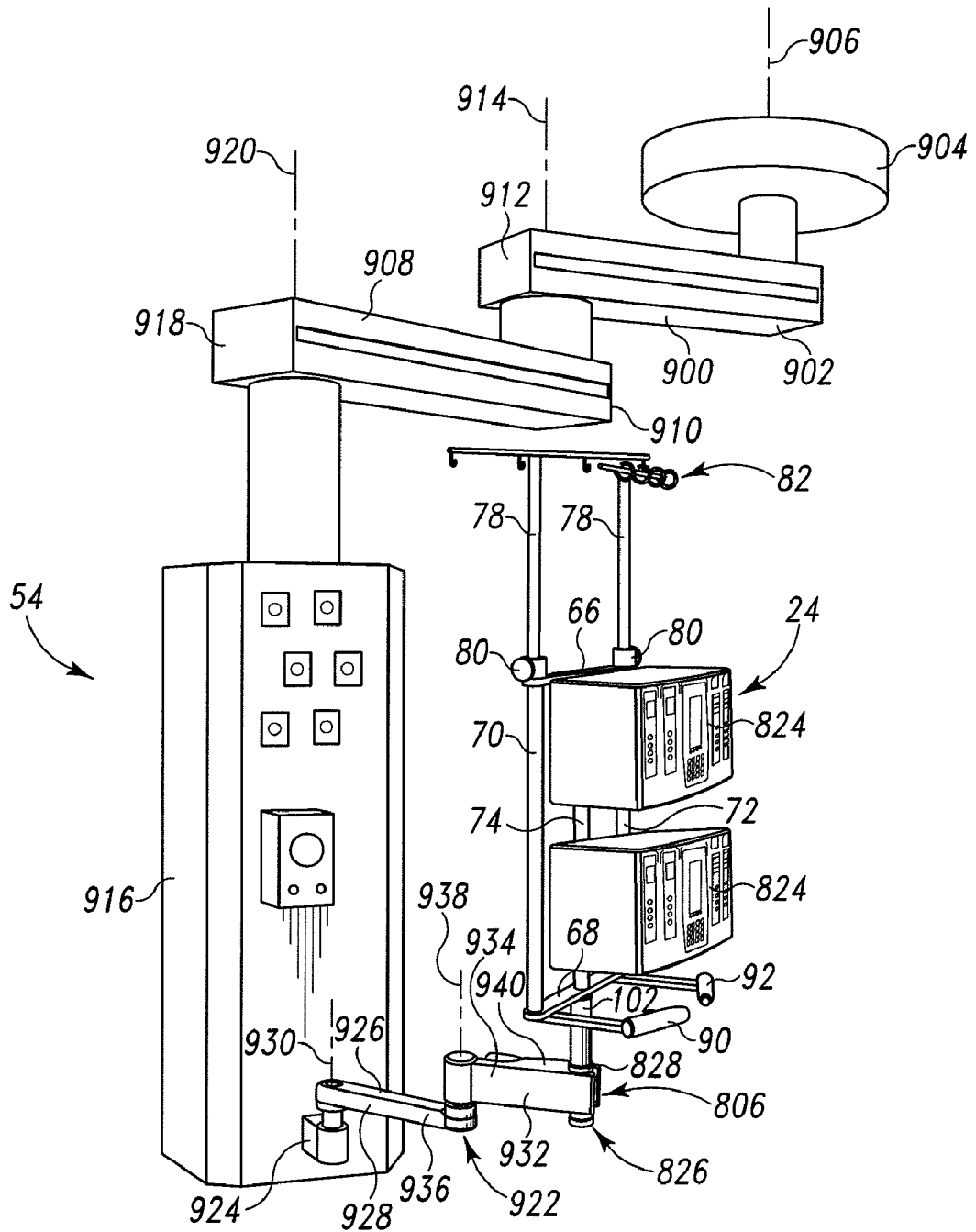
FIG. 20 is a perspective view of the arm system showing a first radial arm having a proximal end pivotally coupled to a ceiling structure, a second radial arm having a proximal end pivotally coupled to a distal end of the first radial arm, a downwardly-extending service head pivotally coupled to a distal end of the second radial arm, an arm extending outwardly from the service head, and a second clamp coupled to a distal end of the arm and clamping the downwardly-extending post of the equipment support.
Figure 21:
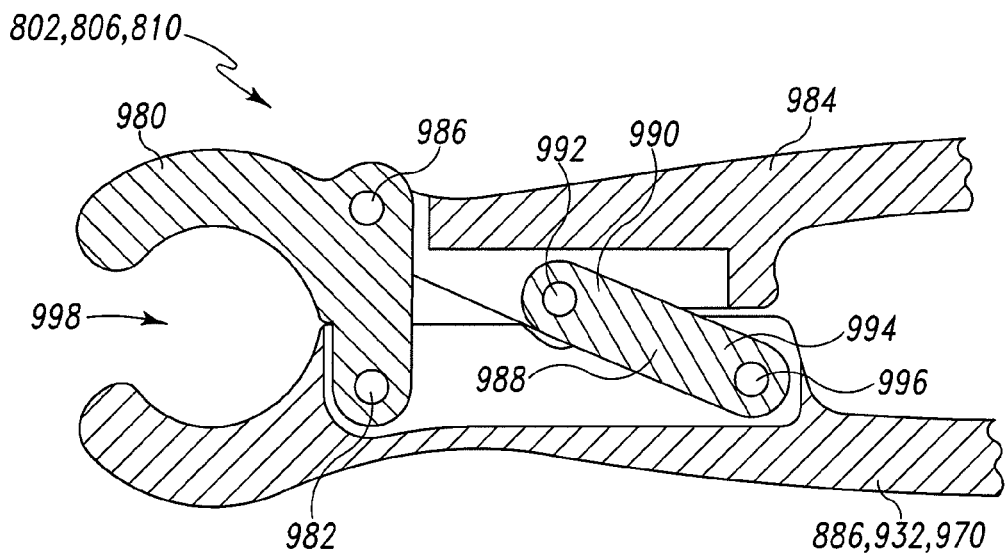
FIG. 21 is a diagrammatic cross sectional view of the clamp of FIGS. 16-19 showing the movable jaw moved to a closed position in response to a handle moving to a closed position.

FIGS. 16-22 show a patient care equipment management system 800 comprising an equipment support 820 that can be transferred from a first device, such as a hospital bed 50 (FIG. 16) having a first clamp 802, to a second device, such as an arm system 54 (FIG. 20) having a second clamp 806, to a third device, such as a wheeled cart 59 (FIG. 19) having a third clamp 810, in any order. The equipment support 820 is similar to equipment support 20 shown in FIG. 1, except that a coupler 826 replaces the coupler 26. The coupler 826 comprises the lower portion 102 of the central post 74 of the equipment support 20. A collar 828 is secured to the lower portion 102 of the central post 74 of the equipment support 820 at a point halfway between its ends. As shown in FIG. 16, the first clamp 802 clamps the lower portion 102 of the central post 74 when the equipment support 820 is carried by the bed 50. As shown in FIG. 20, the second clamp 806 clamps the lower portion 102 of the central post 74 below the collar 828 when the equipment support 820 is carried by the arm system 54. As shown in FIG. 19, the third clamp 810 clamps the lower portion 102 of the central post 74 above the collar 828 when the equipment support 820 is carried by the cart 58. The equipment support 820 is directly transferable from the bed 50 to the cart 58 to the arm system 54 and back to the bed 50, in any order.

It should be understood that although the equipment support 820 is supported by the bed 50, the arm system 54, and the wheeled cart 58 in the illustrated embodiment, the equipment support 820 may very well be supported by other devices, such as a stretcher, a surgical table, a wheel chair, a wheeled stand, and the like, that have clamps for clamping the lower portion 102 of the central post 74 of the equipment support 820. The equipment support 820 carries a plurality of monitors 824 in the illustrated embodiment. However, it should be understood that other medical devices, such as heart monitoring equipment, medical gas delivery equipment, infusion pumps, IV bags, and the like, may very well be carried by the equipment support 20. It will be appreciated that such hospital beds and arm systems are well known and need not be discussed in detail herein. For example, the bed 50 may be of the type marketed by Hill-Rom as TotalCare™ hospital bed and the arm system 54 may be of the type marketed by Hill-Rom as Latitude™ Arm System.

As shown in FIGS. 16, 18, and 19, the bed 50 includes a lower frame 850, an intermediate frame 852, and a patient-support deck 854 supporting a mattress 856. A linkage 858 connects the intermediate frame 852 to the lower frame 850. The linkage 858 is operable to raise, lower, and tilt the intermediate frame 852 and the deck 854 relative to the lower frame 850. The bed 850 includes head and foot-end side rails 860. In the illustrated embodiment, the intermediate frame 852 includes head-end frame member 862, which is configured to extend horizontally beyond the periphery of the deck 854 such that certain items can be mounted thereon, including, for example, push handles 864 having handle grips 865 and corner brackets 866 carrying roller bumpers 868.

Push handles 864 are illustratively configured to respond to urges from a caregiver, including pushing or pulling forces exerted on handles 864. Such pushing or pulling of handles 864 causes handles 864 to act upon respective force sensors interposed between handles 864 and head-end frame member 862. The force sensors may comprise, for example, load cells (not shown) that are housed in the bed 50 and that sense the force applied to handles 864. The load cells send signals to a motorized traction device (not shown) for propelling the bed 50, as is disclosed further in U.S. Publication Number 2002/0088055 A1, incorporated herein by reference. However, it should be understood that push handles 864 may alternatively comprise standard-mount handles, or push handles 864 may be omitted from bed 50.

As shown, for example, in FIG. 16, a bed mount 870 includes a post 872 that extends upwardly from the corner bracket 866 located on a left side 874 of the bed 50 near a head end 876 thereof. Each corner bracket 866 comprises a pair of vertically-spaced flanges 878, 880 defining a bumper-receiving space 882 in which the associated roller bumper 868 is received. A lower portion 884 of the post 872 extends through an opening in the upper flange 878, through a central opening in the roller bumper 868, and finally through an opening in the lower flange 880. An arm 886 has a proximal end 888 coupled to the post 872 for pivoting movement about a pivot axis 890. The first clamp 802 is coupled to a distal end 892 of the arm 886. The first clamp 802 grips the lower portion 102 of the central post 74 when the equipment support 820 is carried by the bed 50 as shown in FIG. 16.

As shown in FIG. 20, the arm system 54 includes a first radial arm 900 that has a proximal end 902 coupled to a ceiling structure 904 for pivoting movement about a first pivot axis 906, a second radial arm 908 having a proximal end 910 coupled to a distal end 912 of the first radial arm 900 for pivoting movement about a second pivot axis 914, and a downwardly-extending service head 916 coupled to a distal end 918 of the second radial arm 908 for pivoting movement about a third pivot axis 920. An arm mount 922 includes a mounting bracket 924 coupled to the service head 916. A first arm 926 has a proximal end 928 coupled to the mounting bracket 924 for pivoting movement about a first pivot axis 930. A second arm 932 has a proximal end 934 coupled to a distal end 936 of the first arm 926 for pivoting movement about a second pivot axis 938. The second clamp 806 is coupled to a distal end 940 of the second arm 932. The second clamp 806 grips the lower portion 102 of the central post 74 below the collar 828 when the equipment support 820 is carried by the arm system 54 as shown in FIG. 20.

As shown in FIGS. 16-19, the cart 59 includes a wheeled base 950 and a post 952 extending upwardly from the base 950. The base 950 has a central hub 954 and five spokes 956 radiating substantially horizontally outwardly from the central hub 954. Casters 958 are coupled to distal ends of the spokes 956. In the illustrated embodiment, the post 952 has a lower portion 960, an upper portion 962 that is offset relative to the lower portion 960, and an intermediate portion 964 that connects the lower and upper portions 960, 962. A pair of handles 966 extend outwardly from an upper end 968 of the post 952. An arm 970 (FIG. 17) extends outwardly from the upper portion 962 of the post 952. The third clamp 810 is coupled to a distal end 972 of the arm 970. The third clamp 810 grips the lower portion 102 of the central post 74 above the collar 828 when the equipment support 820 is carried by the cart 59 as shown in FIG. 19. When the equipment support 820 is carried by the cart 59, the central post 74 of the equipment support 820 is generally axially aligned with the lower portion 960 of the post 952. This ensures that a center of gravity of the equipment support 820 is within a footprint of the cart 59. In some embodiments, the post 952 carrying the clamp 810 is telescoping, in a manner similar to the telescoping column 552 of the cart 58, so that a vertical position of the third clamp 810 is adjustable.

In the illustrated embodiment, the three clamps 802, 806, 810 are substantially identical in construction and operation, except that the first clamp 802 is coupled to the arm 886 of the bed 50, the second clamp 806 is coupled to the arm 932 of the arm system 54, and the third clamp 810 is coupled to the arm 970 (FIG. 17) of the cart 59. As shown diagrammatically in FIGS. 21-22, each clamp 802, 806, 810 includes a movable jaw 980 coupled to the associated arm 886, 932, 970 for pivoting movement about a first pivot pin 982. A handle 984 is coupled to the movable jaw 980 for pivoting movement about a second pivot pin 986. A link 988 has a first end 990 coupled to the handle 984 for pivoting movement about a third pivot pin 992. The link 988 has a second end 994 coupled to the associated arm 886, 932, 970 for pivoting movement about a fourth pivot pin 996.

Figure 22:
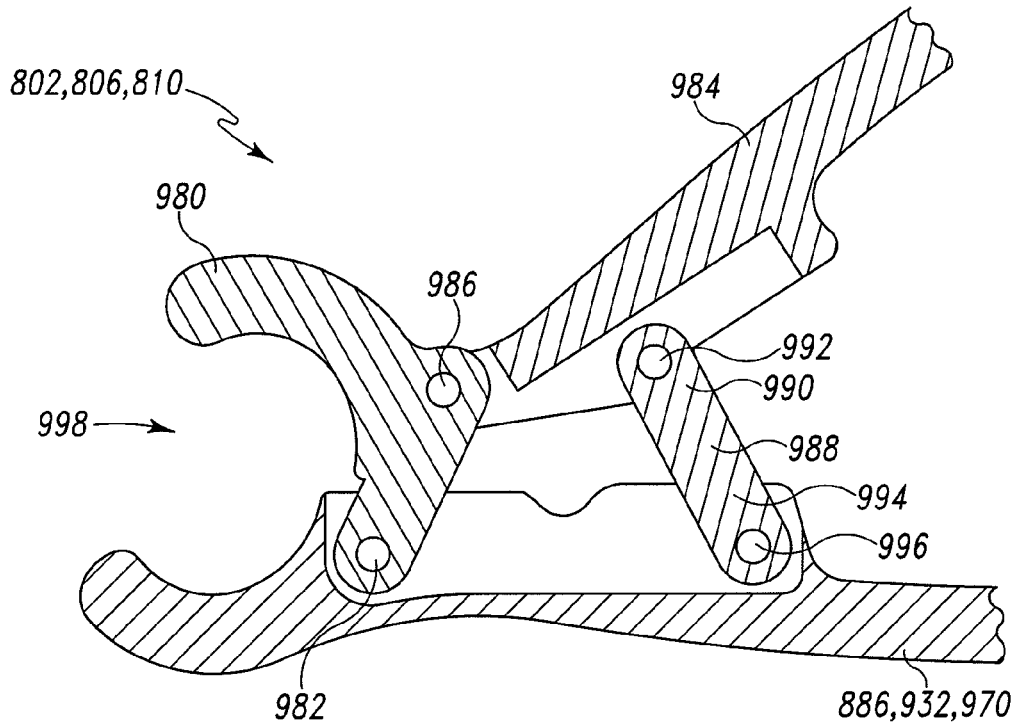
FIG. 22 is a diagrammatic cross sectional view similar to FIG. 21 showing the movable jaw moved to an opened position in response to a handle moving to an opened position.

The movable jaw 980, the handle 984, the link 988, and the associated arm 886, 932, 970 form a four bar linkage such that the movable jaw 980 moves between a closed position (FIG. 21) and an opened position (FIG. 22) as the handle 984 moves between a closed position (FIG. 21) and an opened position (FIG. 22). The lower portion 102 of the central post 74 of the equipment support 820 is received in a post-receiving cavity 998 defined by the arm 886, 932, 970 and the movable jaw 980 when the movable jaw 980 is moved to the opened position. The lower portion 102 of the central post 74 of the equipment support 820 is clamped between the movable jaw 980 and the associated arm 886, 932, 970 when the movable jaw 980 closes after receiving the lower portion 102 of the central post 74 of the equipment support 820 in the post-receiving cavity 998 in response to the handle 984 moving to its closed position.

The handle 984 passes through an over-the-center position as it moves from its opened position to its closed position. The lower portion 102 of the central post 74 of the equipment support 820 exerts an outward force on the movable jaw 980 in a direction that holds the handle 984 in a past-over-the-center closed position. In some embodiments, the clamp 802, 806, 810 includes a latch (not shown) movable between an unlatched position in which the handle 984 is movable between its closed and opened positions and a latched position in which the handle 984 is latched in its closed position.

As shown in FIG. 16, the first clamp 802 clamps the lower portion 102 of the central post 74 of the equipment support 820 below the collar 828 when the equipment support 820 is carried by the bed 50. To transfer the equipment support 820 from the bed 50 to the cart 59, the intermediate frame 852 of the bed 50 is lowered to a position where the third clamp 810 of the cart 59 is located just above the collar 828 as shown in FIG. 18. The handle 984 of the third clamp 810 is then moved to its opened position to open the movable jaw 980 of the third clamp 810 as shown in FIG. 17. The lower portion 102 of the central post 74 of the equipment support 820 is then received in the post-receiving cavity 998 defined by the movable jaw 980 and the arm 970 of the third clamp 810 as shown in FIG. 18 and the handle 984 of the third clamp 810 is moved to its closed position to clamp the lower portion 102 of the central post 74 of the equipment support 820 just above the collar 828. The handle 984 of the first clamp 802 of the bed 50 is then moved to its opened position to release the lower portion 102 of the central post 74 of the equipment support 820 from the bed 50. The cart 59 can then be moved away from the bed 50 with the cart 59 carrying the equipment support 820 as shown in FIG. 19 (or the bed 50 can be moved away from the cart 59 with the cart 59 carrying the equipment support 820).

To transfer the equipment support 820 from the cart 59 to the arm system 54, the service head of the bed 50 is lowered to a position where the second clamp 806 of the arm system 54 is located just below the collar 828 as shown in FIG. 20. The handle 984 of the second clamp 806 is then moved to its opened position to open the movable jaw 980 of the second clamp 806. The lower portion 102 of the central post 74 of the equipment support 820 is then received in the post-receiving cavity 998 defined by the movable jaw 980 and the arm 932 of the second clamp 806 and the handle 984 of the second clamp 806 is moved to its closed position to clamp the lower portion 102 of the central post 74 of the equipment support 820 just below the collar 828. The handle 984 of the third clamp 810 of the cart 59 is then moved to its opened position to release the lower portion 102 of the central post 74 of the equipment support 820 from the cart 59. The cart 59 can then be moved away from the arm system 54 with the arm system 54 carrying the equipment support 820 as shown In FIG. 20 (or the arm system 54 can be moved away from the cart 59 with the arm system 54 carrying the equipment support 820).

To transfer the equipment support 820 from arm system 54 to the bed 50, the intermediate frame 852 of the bed 50 is raised to a position where the first clamp 802 of the bed 50 is located just above the collar 828. The handle 984 of the first clamp 802 of the bed 50 is then moved to its opened position to open the movable jaw 980 of the first clamp 802. The lower portion 102 of the central post 74 of the equipment support 820 is then received in the post-receiving cavity 998 defined by the movable jaw 980 and the arm 886 of the first clamp 802 and the handle 984 of the first clamp 802 is moved to its closed position to clamp the lower portion 102 of the central post 74 of the equipment support 820 just above the collar 828. The handle 984 of the second clamp 806 of the arm system 54 is then moved to its opened position to release the lower portion 102 of the central post 74 of the equipment support 820 from the arm system 54. The arm system 54 can then be moved away from the bed 50 with the bed 50 carrying the equipment support 820 (or the bed 50 can be moved away from the arm system 54 with the bed 50 carrying the equipment support 820). Thus, the equipment support 820 is transferable from the bed 50 to the cart 59 to the arm system 54 and back to the bed 50, in any order.

Figure 23:
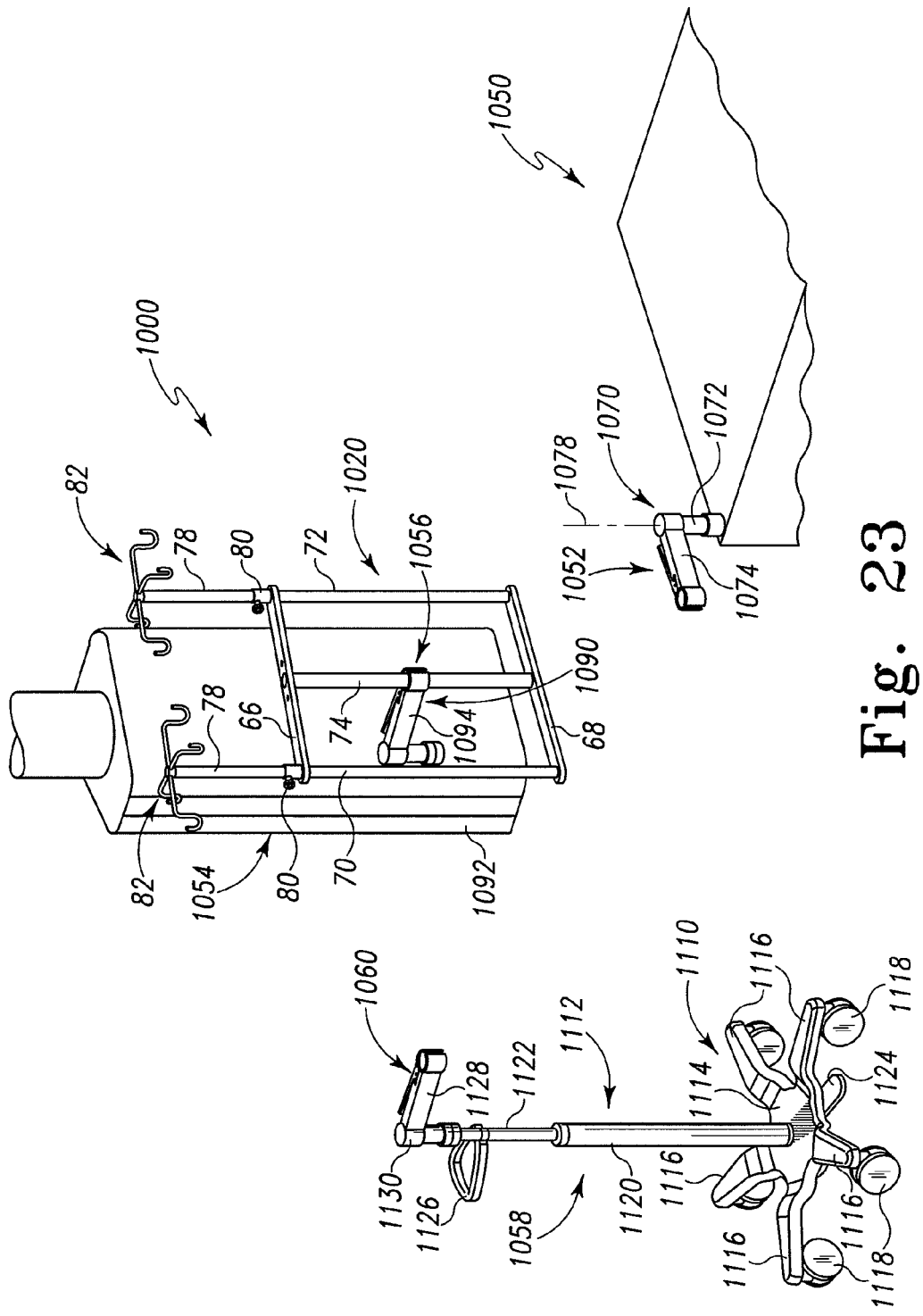
FIG. 23 is a diagrammatic perspective view showing a second embodiment of the patient care equipment management system shown in FIGS. 16-22.

FIG. 23 diagrammatically shows a second embodiment 1000 of the patient care equipment management system 800. The system 1000 comprises an equipment support 1020 that can be transferred from a first device, such as a hospital bed 1050 having a first clamp 1052, to a second device, such as an arm system 1054 having a second clamp 1056, to a third device, such as a wheeled cart 1058 having a third clamp 1060, in any order. The equipment support 1020 is similar to equipment support 820 shown in FIGS. 16-20, except that the central post 74 of the equipment support 1020 does not extend below the lower cross bar 68, and the clamps 1052, 1056, 1060 clamp the central post 74 of the equipment support 1020 between the upper and lower cross bars 66, 68 as shown in FIG. 23 with respect to the arm system 1054.

The bed 1050, diagrammatically shown in FIG. 23, is similar to the bed 50 shown in FIGS. 16, 18, and 19. As shown in FIG. 23, the bed 1050 includes a bed mount 1070 that has a post 1072 that extends upwardly from a corner bracket of the bed 1050, similar to the corner bracket 866 of the bed 50 shown in FIG. 16. An arm 1074 has a proximal end coupled to the post 1072 for pivoting movement about a pivot axis 1078. The first clamp 1052 is coupled to a distal end of the arm 1074. The first clamp 1052 grips the central post 74 of the equipment support 1020 between the upper and lower cross bars 66, 68 when the equipment support 1020 is carried by the bed 1050.

The arm system 1054, diagrammatically shown in FIG. 23, is similar to the arm system 54 shown in FIG. 20. As shown in FIG. 23, the arm system 1054 includes an arm mount 1090 that has a mounting bracket coupled to the service head 1092, similar to the mounting bracket 924 of the arm system 54 shown in FIG. 20. An arm 1094 has a proximal end coupled to the mounting bracket for pivoting movement. The second clamp 1056 is coupled to a distal end of the arm 1094. The second clamp 1056 grips the central post 74 of the equipment support 1020 between the upper and lower cross bars 66, 68 when the equipment support 1020 is carried by the arm system 1054 as shown in FIG. 23.

The cart 1058, diagrammatically shown in FIG. 23, is similar to the cart 58 shown in FIG. 10. As shown in FIG. 23, the cart 1058 includes a wheeled base 1110 and a telescoping column 1112 extending upwardly from the base 1110. The base 1110 has a central hub 1114 and five spokes 1116 radiating substantially horizontally outwardly from the central hub 1114. Casters 1118 are coupled to distal ends of the spokes 1116. In the illustrated embodiment, the column 1112 includes an outer tube 1120 extending upwardly from the central hub 1114 and an inner tube 1122 that telescopes into and out of the outer tube 1120. In the illustrated embodiment, a manually operable locking mechanism, such as a gas spring (not shown), is located inside the outer tube 1120 to releasably secure the inner tube 1122 in a selected vertical position relative to the outer tube 1120. A release pedal 1124 extends outwardly from the base 1110 and is operable to unlock the gas spring to adjust a vertical elevation of the third clamp 1060. A handle 1126 is coupled to the inner tube 1122 just below the third clamp 1060. An arm 1128 extends outwardly from an upper and 1130 of the inner tube 1122. The third clamp 1060 is coupled to a distal end 1132 of the arm 1128. The third clamp 1060 grips the central post 74 of the equipment support 1020 between the upper and lower cross bars 66, 68 when the equipment support 1020 is carried by the cart 1058.

Figure 24:
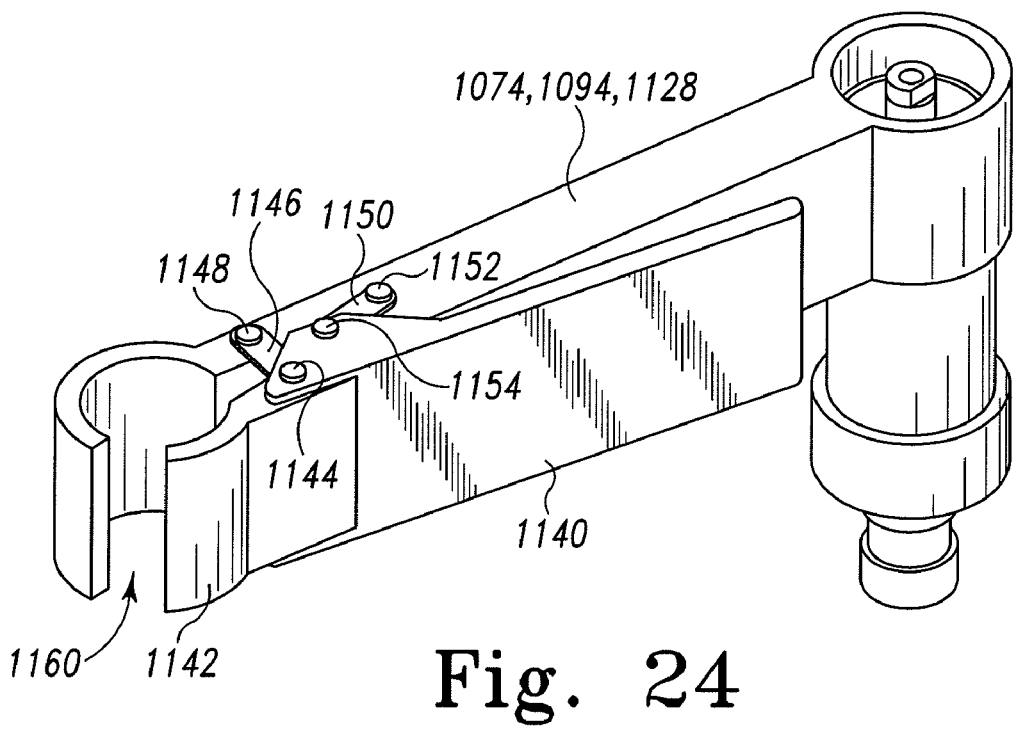
FIG. 24 is a perspective view of the clamp of FIG. 23.

In the illustrated embodiment, the three clamps 1052, 1056, 1060 are substantially identical in construction and operation, except that the first clamp 1052 is coupled to the arm 1074 of the bed 1050, the second clamp 1056 is coupled to the arm 1094 of the arm system 1054, and the third clamp 1060 is coupled to the arm 1128 of the cart 1058. As shown in FIG. 24, each clamp 1052, 1056, 1060 includes a handle 1140, a movable jaw 1142 coupled to the handle 1140 for pivoting movement about a first pivot pin 1144, a pair of first links 1146 having first ends coupled to the movable jaw 1142 and coupled to the handle 1140 for pivoting movement about the first pivot pin 1144 and having second ends coupled to the associated arm 1074, 1094, 1128 for pivoting movement about a second pivot pin 1148, and a pair of second links 1150 having first ends coupled to the associated arm 1074, 1094, 1128 for pivoting movement about a third pivot pin 1152 and having second ends coupled to the handle 1140 for pivoting movement about a fourth pivot pin 1154.

The handle 1140, the first links 1146, the second links 1150 and the associated arm 1074, 1094, 1128 form a four bar linkage such that the movable jaw 1142 moves between a closed position and an opened position as the handle 1140 moves between a closed position and an opened position. The central post 74 of the equipment support 1020 is received in a post-receiving cavity 1160 defined by the movable jaw 1142 and the associated arm 1074, 1094, 1128 when the movable jaw 1142 is moved to the opened position. The central post 74 of the equipment support 1020 is clamped between the movable jaw 1142 and the associated arm 1074, 1094, 1128 when the movable jaw 1142 closes after receiving the central post 74 of the equipment support 1020 in the post-receiving cavity 1170 in response to the handle 1140 moving to its closed position.

In some embodiments, the handle 1142 passes through an over-the-center position as it moves from its opened position to its closed position. The central post 74 of the equipment support 1020 exerts an outward force on the movable jaw 1142 in a direction that holds the handle 1140 in a past-over-the-center closed position. In some other embodiments, the clamp 1052, 1056, 1060 includes a latch (not shown) movable between an unlatched position in which the handle 1140 is movable between its closed and opened positions and a latched position in which the handle 1140 is latched in its closed position. The operation of the system 1000 is similar to the operation of the system 800. The equipment support 820 is directly transferable from the bed 50 to the cart 58 to the arm system 54 and back to the bed 50, in any order.

Figure 25:
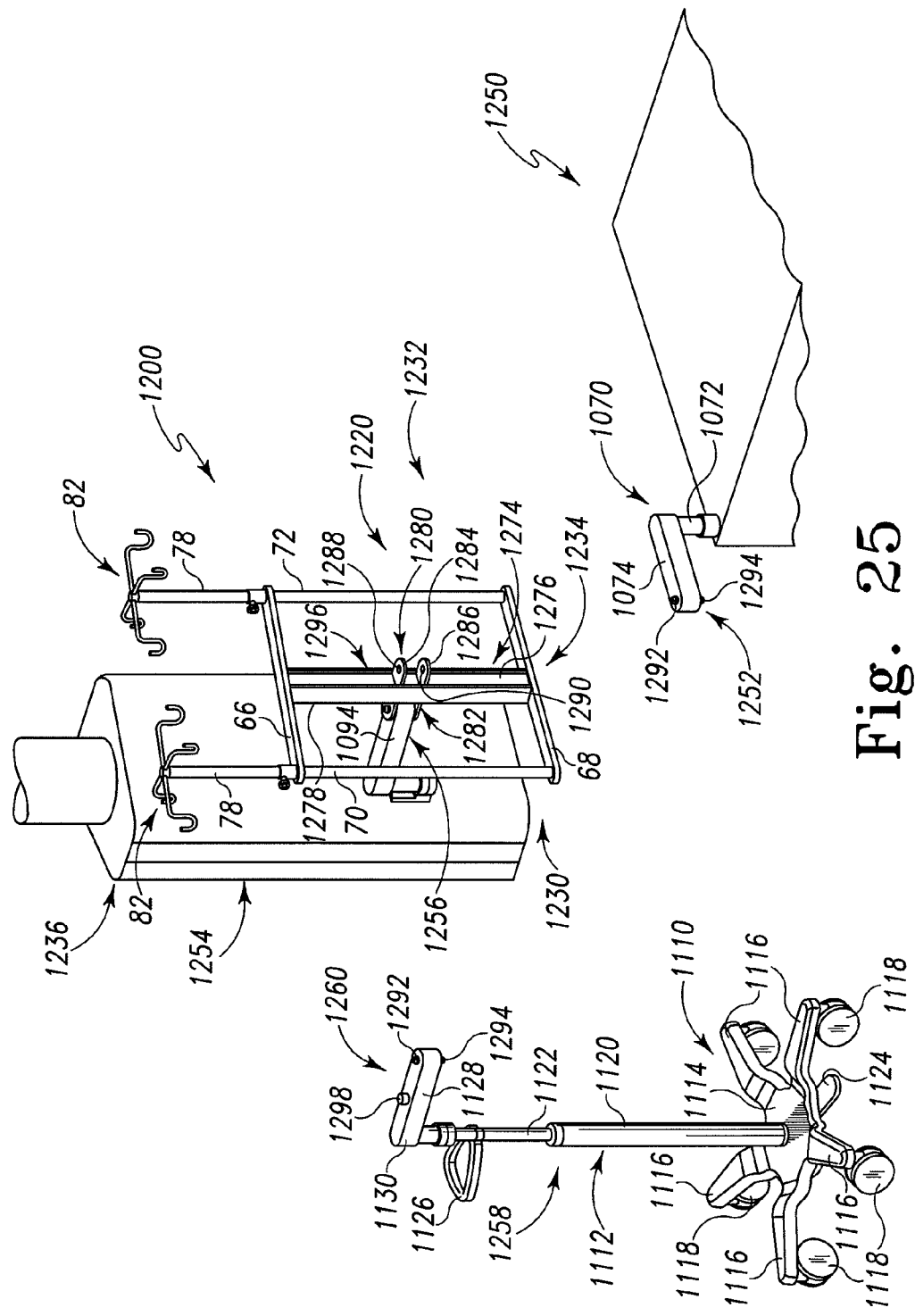
FIG. 25 is a diagrammatic perspective view showing a third embodiment of the patient care equipment management system shown in FIGS. 16-22.

FIG. 25 diagrammatically shows a third embodiment 1200 of the patient care equipment management system 800. The system 1200 comprises an equipment support 1220 that can be transferred from a first device, such as a hospital bed 1250 having a first clamp 1252, to a second device, such as an arm system 1254 having a second clamp 1256, to a third device, such as a wheeled cart 1258 having a third clamp 1260, in any order. The equipment support 1220 is similar to equipment support 1020 shown in FIG. 23, except that a central column 1274 replaces the central post 74. As shown diagrammatically in FIG. 25, the central post 1274 of the equipment support 1220 does not extend below the lower cross bar 68. The central column 1074 has a first vertical track 1276 on a front side 1234 of the equipment support 1220 and a second vertical track 1278 on a rear side 1236 of the equipment support 1220.

A first clevis 1280 rides in the first track 1276 on the front side 1234 of the equipment support 1220. A second clevis 1282 rides in the second track 1278 on the rear side 1236 of the equipment support 1220. The height of each clevis 1280, 1282 is changed by depressing an associated lever 1296. When the lever 1296 is depressed, the associated clevis 1280, 1282 is unlocked to move up or down in the associated track 1276, 1278. The clevis 1280, 1282 is again locked in place when the lever 1296 is released. Each clevis 1280, 1282 includes a pair of vertically-spaced upper and lower flanges 1284, 1286 that extend outwardly from the column 1274. The flanges 1284, 1286 have vertically aligned holes 1288, 1290 for receiving a pair of oppositely-disposed retractable pins 1292, 1294 of the associated clamp 1252, 1256, 1260.

Figure 26:
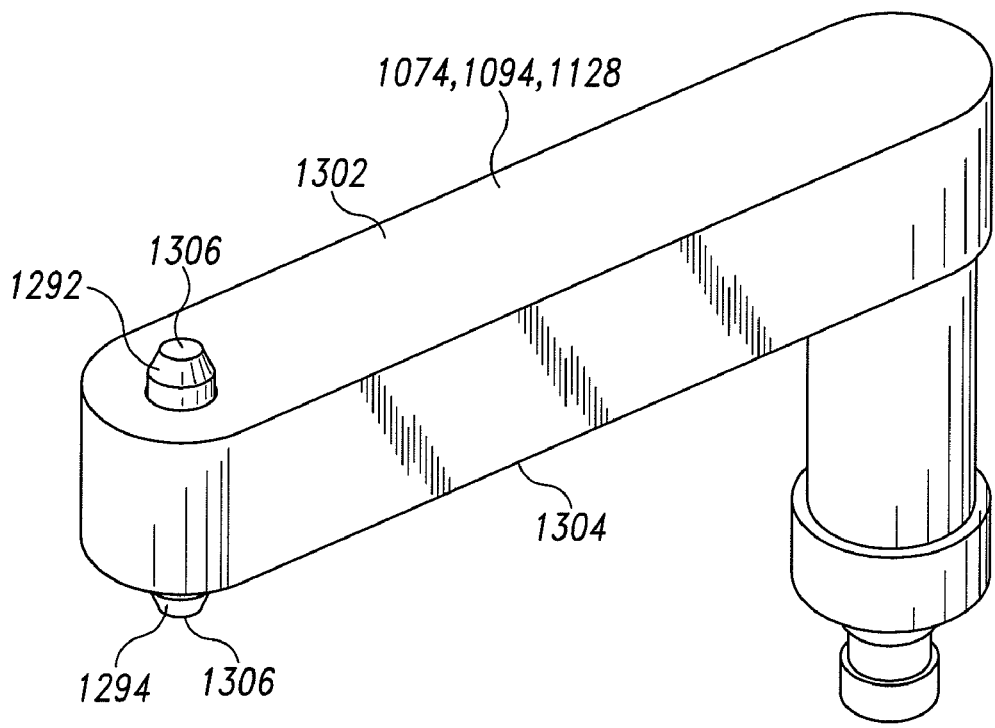
FIG. 26 is a perspective view of the clamp of FIG. 25.

In the embodiment illustrated in FIG. 25, the three clamps 1252, 1256, 1260 are substantially identical in construction and operation, except that the first clamp 1252 is coupled to the arm 1074 of the bed 1250, the second clamp 1256 is coupled to the arm 1094 of the arm system 1254, and the third clamp 1260 is coupled to the arm 1128 of the cart 1258. As shown in FIG. 26, each clamp 1252, 1256, 1260 comprises oppositely-disposed upper and lower retractable pins 1292, 1294 that are movable relative to the associated arm 1074, 1094, 1128 between respective retracted and extended positions in response to movement of a manual input 1298 between a releasing position and a locking position. In some embodiments, each clamp 1252, 1256, 1260 comprises a latch movable between an unlatched position in which the manual input 1298 is movable between the releasing and locking positions and a latched position in which the manual input 1298 is latched in the locking position.

The top and bottom flanges 1284, 1286 of each clevis 1280, 1282 defines an arm-receiving space in which the associated arm 1074, 1094, 1128 is received. A vertical spacing between the top and bottom flanges 1284, 1286 (FIG. 25) of each clevis 1280, 1282 is slightly greater than a vertical spacing between the top and bottom sides 1302, 1304 (FIG. 26) of each arm 1074, 1094, 1128. The pins 1292, 1294 are received in the holes 1288, 1290 in the flanges 1284, 1286 of the associated clevis 1280, 1282. For example, as shown in FIG. 25, the pins 1292, 1294 of the second clamp 1256 of the arm system 1254 are received in the holes 1288, 1290 in the flanges 1284, 1286 of the second clevis 1282 of the equipment support 1220.

In the illustrated embodiment, the pins 1292, 1294 are disposed on top and bottom sides 1302, 1304 (FIG. 26) of the associated arm 1074, 1094, 1128. The top pin 1292 protrudes from the top side 1302 of the associated arm 1074, 1094, 1128 when the top pin 1292 is disposed in its extended position. The bottom pin 1294 protrudes from the bottom side 1304 of the associated arm 1074, 1094, 1128 when the bottom pin 1294 is disposed in its retracted position. Head portions 1306 of the pins 1292, 1294 are substantially flush with the top and bottom sides 1302, 1304 of the associated arm 1074, 1094, 1128 when the pins 1292, 1294 are in their respective retracted positions.

The bed 1250, diagrammatically shown in FIG. 25, is similar to the bed 1050 shown in FIG. 23 except that the clamp 1252 is coupled to the arm 1074, instead of the clamp 1052. The pins 1292, 1294 of the clamp 1252 are received in respective holes 1288, 1290 in the flanges 1284, 1286 of the first clevis 1280 when the equipment support 1220 is carried by the bed 1250. The arm system 1254 is similar to the arm system 1054 shown in FIG. 23, except that the clamp 1256 is coupled to the arm 1094 instead of the clamp 1056. The pins 1292, 1294 of the clamp 1256 are received in respective holes 1288, 1290 in the flanges 1284, 1286 of the second clevis 1282 when the equipment support 1220 is carried by the arm system 1254 as shown in FIG. 25. The cart 1258 is similar to the cart 1058 shown in FIG. 23, except that the clamp 1260 is coupled to the arm 1128 instead of the clamp 1060. The pins 1292, 1294 of the clamp 1260 are received in respective holes 1288, 1290 in the flanges 1284, 1286 of the first clevis 1280 when the equipment support 1220 is carried by the cart 1258. The operation of the system 1200 is generally similar to the operation of the systems 800, 1000.

The first clamp 1252 clamps the first clevis 1280 of the equipment support 1220 when the equipment support 1220 is carried by the bed 1250. When the equipment support 1220 is carried by the bed 1250, the arm 1074 of the bed 1250 is received between the flanges 1284, 1286 of the first clevis 1280 and the pins 1292, 1294 of the first clamp 1252 of the bed 1250 are received in the holes 1288, 1290 in the flanges 1284, 1286 of the first clevis 1280. To transfer the equipment support 1220 from the bed 1250 to the arm system 1254, the pins 1292, 1294 of the second clamp 1256 of the arm system 1254 are retracted and the arm 1094 of the arm system 1254 is positioned between the flanges 1284, 1286 of the second clevis 1282 so that the pins 1292, 1294 of the second clamp 1256 are aligned with the holes 1288, 1290 in the flanges 1284, 1286 of the second clevis 1282. The pins 1292, 1294 of the second clamp 1256 of the arm system 1256 are then extended so that the pins 1292, 1294 of the second clamp 1256 are received in the holes 1288, 1290 in the flanges 1284, 1286 of the second clevis 1282. The pins 1292, 1294 of the first clamp 1252 of the bed 1250 are then retracted to free the equipment support 1220 from the bed 1250. The arm system 1254 can then be moved away from the bed 1250 with the arm system 1254 carrying the equipment support 1220 as shown in FIG. 25 (or the bed 1250 can be moved away from the arm system 1254 with the arm system 1254 carrying the equipment support 1220).

To transfer the equipment support 1220 from the arm system 1254 to the cart 1258, the pins 1292, 1294 of the third clamp 1260 of the cart 1258 are retracted and the arm 1128 of the cart 1258 is positioned between the flanges 1284, 1286 of the first clevis 1280 so that the pins 1292, 1294 of the third clamp 1260 are aligned with the holes 1288, 1290 in the flanges 1284, 1286 of the first clevis 1280. The pins 1292, 1294 of the third clamp 1260 of the cart 1258 are then extended so that the pins 1292, 1294 of the third clamp 1260 are received in the holes 1288, 1290 in the flanges 1284, 1286 of the first clevis 1280. The pins 1292, 1294 of the second clamp 1256 of the arm system 1254 are then retracted to free the equipment support 1220 from the arm system 1254. The cart 1258 can then be moved away from the arm system 1254 with the cart 1258 carrying the equipment support 1220 (or the arm system 1254 can be moved away from the cart 1258 with the cart 1258 carrying the equipment support 1220).

To transfer the equipment support 1220 from the cart 1258 to the bed, the pins 1292, 1294 of the first clamp 1252 of the bed 1250 are retracted and the arm 1074 of the bed 1250 is positioned between the flanges 1284, 1286 of the second clevis 1282 so that the pins 1292, 1294 of the first clamp 1252 are aligned with the holes 1288, 1290 in the flanges 1284, 1286 of the second clevis 1282. The pins 1292, 1294 of the first clamp 1252 of the bed 1250 are then extended so that the pins 1292, 1294 of the first clamp 1252 are received in the holes 1288, 1290 in the flanges 1284, 1286 of the second clevis 1282. The pins 1292, 1294 of the third clamp 1260 of the cart 1258 are then retracted to free the equipment support 1220 from the cart 1258. The cart 1258 can then be moved away from the bed 1250 with the bed 1250 carrying the equipment support 1220 (or the bed 1250 can be moved away from the cart 1258 with the bed 1250 carrying the equipment support 1220).

Although the invention has been described in detail with reference to certain illustrative embodiments, variations and modifications exist with the scope and spirit of this disclosure as described and defined in the following claims.

The invention claimed is:

1. A patient care equipment support transferable between a first device having a first coupling member and a second device having a second coupling member, the equipment support comprising:

an equipment supporting portion configured to support patient care equipment, and a coupler coupled to the equipment supporting portion and having first and second clamps, wherein the first clamp includes a first handle, the first clamp being configured to grip the first coupling member when the first handle is moved to a locking position, and wherein the second clamp includes a second handle, the second clamp being configured to grip the second coupling member when the second handle is moved to a locking position, the first and second handles moveable independently of one another, wherein the coupler further includes a mounting block, a first link and a second link, the first clamp further includes a first jaw, the first handle coupled to a first side of the mounting block and the first link coupled to the first jaw and coupled to the first handle such that the first jaw moves between an opened position and a closed position as the first handle moves between a releasing position and the locking position, the second clamp further includes a second jaw, the second handle coupled to a second side of the mounting block and the second link coupled to the second jaw and coupled to the second handle such that the second jaw moves between an opened position and a closed position as the second handle moves between a releasing position and the locking position, and wherein the coupler comprises a post that extends downwardly from the equipment supporting portion, and the mounting block is coupled to the post, and wherein the first jaw is coupled to the first side of the mounting block for pivoting movement about a first pivot pin, the first handle is coupled to the first side of the mounting block for pivoting movement about a second pivot pin, and the first link has a first end coupled to the first jaw for pivoting movement about a third pivot pin, the first link has a second end coupled to the first handle for pivoting movement about a fourth pivot pin, the second jaw is coupled to the second side of the mounting block for pivoting movement about a fifth pivot pin, the second handle is coupled to the second side of the mounting block for pivoting movement about a sixth pivot pin, the second link has a first end coupled to the second jaw for pivoting movement about a seventh pivot pin, and the second link has a second end coupled to the second handle for pivoting movement about an eighth pivot pin.

2. The equipment support of claim 1, wherein the coupler comprises a post that extends downwardly from the equipment supporting portion, and the first and second clamps are coupled to the post on first and second sides of the post.

3. The equipment support of claim 1, wherein the first clamp is closeable to grip the first coupling member when the equipment support is carried by the first device, and the second clamp is closeable to grip the second coupling member, and the equipment support is transferable from the first device to the second device when the first clamp releases the first coupling member allowing the first device to move away from the second device.

4. The equipment support of claim 1, wherein the mounting block, the first jaw, the first handle, and the first link form a first four bar linkage, and the mounting block, the second jaw, the second handle, and the second link form a second four bar linkage.

5. The equipment support of claim 1, wherein the first coupling member of the first device comprises a first post that is configured to be received in a first post-receiving cavity defined by the first jaw and the mounting block when the first jaw is moved to the opened position, and the first post is clamped between the first jaw and the mounting block when the first jaw moves to the closed position after receiving the first post in the first post-receiving cavity in response to the first handle moving to the locking position.

6. The equipment support of claim 5, wherein a second post-receiving cavity is defined by the second jaw and the mounting block when the second jaw is moved to the opened position, and the second jaw moves to the closed position in response to the second handle moving to the locking position.

7. The equipment support of claim 6, further comprising a lock configured such that when a post is received in one of the post-receiving cavities and the associated handle is moved to the locking position, said post is locked to the equipment support coupler, and such that when a second post is received in the second of the post-receiving cavity, both of the handles are unlocked so that respective engagements of both posts and the equipment support coupler are releasable.

8. The equipment support of claim 7, wherein the lock comprises a first slider and a second slider which are both spring biased such that a first tab of the first slider projects into the second post-receiving cavity and a first hook of the first slider engages the third pivot pin to normally lock the first handle in the locking position and such that a second tab of the second slider projects into the first post-receiving cavity and a second hook of the second slider engages the seventh pivot pin to normally lock the second handle in the locking position.

9. The equipment support of claim 8, wherein, when the first post is received in the first post-receiving cavity, the first post engages the second tab to shift the second slider against a spring force to disengage the second hook from engagement with the seventh pivot pin to unlock the second handle.

10. The equipment support of claim 8, wherein each slider has two slots through which the first and fifth pivot pins extend so that the sliders can shift between their respective latching positions and unlatching positions.

11. The equipment support of claim 8, wherein the lock further comprises a spring that is situated in a state of compression between the first and second tabs to bias the first and second sliders in opposite directions so that the first tab projects into the second post-receiving cavity and the second tab projects into the first post-receiving cavity.

12. The equipment support of claim 6, further comprising a lock that is movable to the first side when the first handle is in the locking position to lock the first handle in the locking position and to lock the first jaw in the closed position and to unlock the second handle and the lock is movable to the second side when the second handle is in the locking position to lock the second handle in the locking position and to lock the second jaw in the closed position and to unlock the first handle.

13. The equipment support of claim 12, wherein the lock is not movable to the first side when the first handle is the releasing position and the lock is not movable to the second side when the second handle is the releasing position.

14. The equipment support of claim 1, wherein the equipment supporting portion comprises an upper cross bar, a lower cross bar, a pair of outer posts extending between the upper and lower cross bars adjacent to the opposite ends thereof and a central post extending between the upper and lower cross bars between the two outer posts, and the first and second clamps are coupled to a lower portion of the central post that extends below the lower cross bar.

15. The equipment support of claim 14, wherein each outer post comprises a first portion and a second portion that telescopes into and out of the first portion and a lock movable between a releasing position allowing the second portion to telescope into and out of the first portion and a locking position preventing the second portion from telescoping relative to the first portion.

16. The equipment support of claim 15, wherein each outer post further comprises a plurality of IV bag hooks coupled to an upper end of the second portion.

17. The equipment support of claim 14, further comprising a pair of handles extending forwardly from the lower cross bar adjacent to the outer posts.

* * * * *